US007309497B2

(12) United States Patent
Rimpler et al.

(10) Patent No.: US 7,309,497 B2
(45) Date of Patent: Dec. 18, 2007

(54) INJECTABLE PHARMACEUTICAL COMPOSITION FOR SYSTEMATIC ADMINISTRATION OF PHARMACOLOGICALLY ACTIVE INGREDIENTS

(75) Inventors: Stephan Rimpler, Hilden (DE); Sabine Grapatin, Langenfeld (DE); Cliff Krein, Overath (DE); Markus Thelen, Monheim (DE)

(73) Assignee: Schwarz Pharma AG, Monheim (DE)

(*) Notice: Subject to any disclaimer, the term of this patent is extended or adjusted under 35 U.S.C. 154(b) by 279 days.

(21) Appl. No.: 10/344,863

(22) PCT Filed: Aug. 21, 2001

(86) PCT No.: PCT/EP01/09596

§ 371 (c)(1),
(2), (4) Date: Feb. 11, 2003

(87) PCT Pub. No.: WO02/15937

PCT Pub. Date: Feb. 28, 2002

(65) Prior Publication Data

US 2003/0180332 A1 Sep. 25, 2003

(30) Foreign Application Priority Data

Aug. 24, 2000 (DE) ............... 100 41 478

(51) Int. Cl.
*A61F 13/00* (2006.01)
*A61K 9/00* (2006.01)

(52) U.S. Cl. .................... 424/422; 424/400

(58) Field of Classification Search ........... 424/422, 424/400
See application file for complete search history.

(56) References Cited

U.S. PATENT DOCUMENTS 3,637,740 A  1/1972 Sarges ............... 260/326.5

(Continued)

FOREIGN PATENT DOCUMENTS

CA  2 532 804  2/2005

(Continued)

OTHER PUBLICATIONS

Bartoszyk, 1998, "Anxiolytic Effects", Life Science, vol. 62, No. 7, pp. 649-663.

(Continued)

*Primary Examiner*—Humera N. Sheikh
(74) *Attorney, Agent, or Firm*—Harness, Dickey & Pierce PLC (57) ABSTRACT

The invention relates to novel pharmaceutical compositions for the systemic administration of pharmacologically active ingredients. The invention relates in particular to an injectable pharmaceutical composition comprising (a) a pharmacologically active ingredient in a solid phase, (b) a vehicle consisting substantially of polyol fatty acid esters with a degree of esterification of over 80%, and (c) a wetting agent consisting substantially of polyol fatty acid esters with a monoester proportion of over 60%. The inventive composition is used for the systemic administration of numerous pharmacologically active ingredients, whereby the ingredients are released from the pharmaceutical composition over a period of at least 12, preferably at least 24 hours.

29 Claims, 6 Drawing Sheets

U.S. PATENT DOCUMENTS

| | | | |
|---|---|---|---|
| 3,954,983 A * | 5/1976 | Albrecht et al. | 514/222.8 |
| 3,972,995 A | 8/1976 | Tsuk et al. | 424/28 |
| 4,054,488 A | 10/1977 | Marbach | 195/1.8 |
| 4,056,635 A | 11/1977 | Glen et al. | |
| 4,117,156 A | 9/1978 | Loewe et al. | 424/302 |
| 4,320,148 A | 3/1982 | DeMarinis | 424/330 |
| 4,410,519 A | 10/1983 | Seiler et al. | 424/226 |
| 4,452,808 A | 6/1984 | Gallagher | 424/274 |
| 4,465,692 A | 8/1984 | Horn | |
| 4,501,890 A | 2/1985 | Nichols et al. | 514/267 |
| 4,540,691 A | 9/1985 | Horn | 514/211 |
| 4,542,135 A | 9/1985 | Kobel et al. | 514/250 |
| 4,556,676 A | 12/1985 | Welch et al. | 514/554 |
| 4,564,364 A | 1/1986 | Zaffaroni et al. | 604/897 |
| 4,564,628 A * | 1/1986 | Horn | 514/438 |
| 4,657,925 A | 4/1987 | Horn | 514/438 |
| 4,743,618 A | 5/1988 | Horn | 514/438 |
| 4,755,535 A | 7/1988 | Minaskanian et al. | 514/947 |
| 4,772,933 A | 9/1988 | Schade | |
| 4,801,586 A | 1/1989 | Minaskanian et al. | 514/212 |
| 4,808,414 A | 2/1989 | Peck et al. | 424/449 |
| 4,824,860 A | 4/1989 | Owen | 514/418 |
| 4,840,796 A | 6/1989 | Sweet et al. | 424/448 |
| 4,843,086 A | 6/1989 | Griss et al. | 514/367 |
| 4,847,253 A * | 7/1989 | Buonamici et al. | 514/253.02 |
| 4,863,951 A | 9/1989 | Peglion et al. | 514/422 |
| 4,863,970 A | 9/1989 | Patel et al. | 514/784 |
| 4,865,920 A | 9/1989 | Sweet | 428/447 |
| 4,874,768 A | 10/1989 | Huth et al. | 514/288 |
| 4,879,275 A | 11/1989 | Minaskanian et al. | 514/24 |
| 4,882,352 A | 11/1989 | Horn | 514/438 |
| 4,882,377 A | 11/1989 | Sweet et al. | 524/267 |
| 4,885,308 A | 12/1989 | Horn | |
| 4,886,545 A | 12/1989 | Peck et al. | 71/88 |
| 4,886,783 A | 12/1989 | Minaskanian et al. | 574/29 |
| 4,886,812 A | 12/1989 | Griss et al. | 514/321 |
| 4,898,920 A | 2/1990 | Lee et al. | 525/477 |
| 4,902,676 A | 2/1990 | Peck et al. | 514/29 |
| 4,908,208 A | 3/1990 | Lee et al. | 424/409 |
| 4,915,950 A | 4/1990 | Miranda et al. | 424/448 |
| 4,917,896 A | 4/1990 | Peck et al. | 424/449 |
| 4,920,101 A | 4/1990 | Minaskanian et al. | 514/24 |
| 4,931,270 A | 6/1990 | Horn et al. | 424/1.1 |
| 4,951,657 A | 8/1990 | Pfister et al. | 128/156 |
| 4,973,468 A | 11/1990 | Chiang et al. | 424/449 |
| 4,992,422 A | 2/1991 | Minaskanian et al. | 514/24 |
| 4,996,199 A | 2/1991 | Minaskanian et al. | 514/167 |
| 4,996,226 A | 2/1991 | Horn | |
| 5,017,573 A | 5/1991 | Kon et al. | 514/218 |
| 5,034,386 A | 7/1991 | Peck et al. | 514/212 |
| 5,043,441 A | 8/1991 | Peck et al. | 540/526 |
| 5,066,655 A | 11/1991 | Olsson | 514/261 |
| 5,069,909 A | 12/1991 | Sharma et al. | 424/449 |
| 5,071,645 A | 12/1991 | Johnson et al. | 424/486 |
| 5,071,875 A | 12/1991 | Horn et al. | 514/613 |
| 5,073,544 A | 12/1991 | Peck et al. | 514/24 |
| 5,091,186 A | 2/1992 | Miranda et al. | 424/448 |
| 5,108,991 A | 4/1992 | Rajadhyaksha | 514/29 |
| 5,117,830 A | 6/1992 | McAfee et al. | 128/654 |
| 5,118,676 A | 6/1992 | Minaskanian et al. | 514/183 |
| 5,118,692 A | 6/1992 | Peck | 514/317 |
| 5,118,704 A | 6/1992 | Minaskanian et al. | 514/416 |
| 5,118,845 A | 6/1992 | Peck et al. | 564/215 |
| 5,124,157 A | 6/1992 | Colley et al. | 424/448 |
| 5,142,044 A | 8/1992 | Minaskanian et al. | 540/529 |
| 5,147,916 A | 9/1992 | Sweet | 524/266 |
| 5,151,446 A | 9/1992 | Horn et al. | 514/617 |
| 5,162,410 A | 11/1992 | Sweet | 524/588 |
| 5,176,643 A | 1/1993 | Kramer et al. | |
| 5,177,112 A | 1/1993 | Horn | 514/654 |
| 5,186,939 A | 2/1993 | Cleary et al. | 424/448 |
| 5,204,339 A | 4/1993 | Minaskanian et al. | 514/182 |
| 5,214,156 A | 5/1993 | Andersson et al. | |
| 5,218,113 A | 6/1993 | Minaskanian et al. | 540/485 |
| 5,225,198 A | 7/1993 | Sharma et al. | 424/443 |
| 5,232,702 A | 8/1993 | Pfister et al. | 424/448 |
| 5,234,690 A | 8/1993 | Chiang et al. | 424/448 |
| 5,234,945 A * | 8/1993 | Belluzzi | 514/438 |
| 5,234,959 A | 8/1993 | Minaskanian et al. | 514/778 |
| 5,246,997 A | 9/1993 | Sweet | |
| 5,252,334 A | 10/1993 | Chiang et al. | 424/448 |
| 5,252,335 A | 10/1993 | Chiang | 424/449 |
| 5,256,398 A | 10/1993 | McAfee et al. | 424/9 |
| 5,256,661 A | 10/1993 | Horn | 514/248 |
| 5,271,940 A | 12/1993 | Cleary et al. | 424/448 |
| 5,273,755 A | 12/1993 | Venktrama et al. | 424/448 |
| 5,273,756 A | 12/1993 | Fallon et al. | 424/448 |
| 5,273,757 A | 12/1993 | Jaeger et al. | 424/448 |
| 5,274,003 A | 12/1993 | Peck et al. | 514/651 |
| 5,274,346 A | 12/1993 | Izu et al. | 333/184 |
| 5,278,150 A | 1/1994 | Olsson et al. | 514/46 |
| 5,300,299 A | 4/1994 | Sweet et al. | 424/448 |
| 5,308,625 A | 5/1994 | Wong et al. | 424/449 |
| 5,310,731 A | 5/1994 | Olsson et al. | 514/46 |
| 5,358,971 A | 10/1994 | Peck et al. | 514/651 |
| 5,382,596 A | 1/1995 | Sleevi et al. | 514/459 |
| 5,393,529 A | 2/1995 | Hoffmann et al. | |
| 5,430,056 A | 7/1995 | Peck | 514/470 |
| 5,442,117 A | 8/1995 | Stahly et al. | 564/304 |
| 5,456,745 A | 10/1995 | Roreger et al. | |
| 5,462,947 A | 10/1995 | Svensson et al. | 514/317 |
| 5,464,632 A | 11/1995 | Cousin et al. | 424/465 |
| 5,470,848 A | 11/1995 | Minaskanian et al. | 514/182 |
| 5,472,946 A | 12/1995 | Peck et al. | 514/29 |
| 5,477,857 A | 12/1995 | McAfee et al. | 128/654 |
| 5,486,611 A | 1/1996 | Lin et al. | 546/62 |
| 5,496,843 A | 3/1996 | Nagata et al. | 514/411 |
| 5,519,034 A | 5/1996 | Kozlik et al. | 514/307 |
| 5,532,278 A | 7/1996 | Aberg et al. | 514/617 |
| 5,545,755 A | 8/1996 | Lin et al. | 564/428 |
| 5,554,381 A | 9/1996 | Roos et al. | 424/449 |
| 5,565,566 A | 10/1996 | Olsson | 544/277 |
| 5,601,839 A | 2/1997 | Quan et al. | |
| 5,614,518 A | 3/1997 | Leeson et al. | 514/234.5 |
| 5,633,376 A | 5/1997 | Thurkauf et al. | 544/360 |
| 5,656,286 A | 8/1997 | Miranda et al. | 424/449 |
| 5,658,955 A | 8/1997 | Hitzig | 514/654 |
| 5,658,975 A | 8/1997 | Ulman et al. | |
| 5,663,167 A | 9/1997 | Pickar et al. | 514/225.8 |
| 5,670,164 A | 9/1997 | Meconi et al. | |
| 5,670,501 A | 9/1997 | Peck et al. | 514/234.2 |
| 5,677,346 A | 10/1997 | Aberg et al. | 51/617 |
| 5,681,956 A | 10/1997 | Thurkauf et al. | 544/295 |
| 5,688,524 A | 11/1997 | Hsu et al. | 424/449 |
| 5,696,128 A | 12/1997 | Cincotta et al. | 514/284 |
| 5,756,483 A | 5/1998 | Merkus | |
| 5,771,890 A | 6/1998 | Tamada | 128/635 |
| 5,807,570 A | 9/1998 | Chen et al. | 424/449 |
| 5,807,855 A | 9/1998 | Bogeso et al. | 514/469 |
| 5,807,868 A | 9/1998 | Sargent et al. | 514/307 |
| 5,834,010 A | 11/1998 | Quan et al. | |
| 5,840,336 A | 11/1998 | Hsu et al. | |
| 5,843,472 A | 12/1998 | Ma et al. | 424/449 |
| 5,872,127 A | 2/1999 | Cincotta et al. | 514/288 |
| 5,872,133 A | 2/1999 | Cincotta et al. | 514/323 |
| 5,876,746 A | 3/1999 | Jona et al. | 424/449 |
| 5,877,180 A | 3/1999 | Linden et al. | 514/266 |
| 5,879,701 A | 3/1999 | Audett et al. | 424/448 |
| 5,891,461 A | 4/1999 | Jona et al. | 424/449 |
| 5,891,891 A | 4/1999 | Benincasa | 514/300 |
| 5,902,603 A | 5/1999 | Chen et al. | 424/449 |
| 5,905,083 A | 5/1999 | Cincotta et al. | 514/288 |
| 5,906,830 A | 5/1999 | Farinas et al. | 424/448 |
| 5,980,932 A | 11/1999 | Chiang et al. | 424/448 |

| | | | | | | |
|---|---|---|---|---|---|---|
| 5,981,524 | A | 11/1999 | Peck et al. ............... 514/234.2 | EP | 0524775 | 1/1993 |
| 6,001,861 | A | 12/1999 | Oertel et al. ............... 514/367 | EP | 1256340 | 11/2002 |
| RE36,494 | E | 1/2000 | Olsson et al. ................ 514/46 | ES | 2005163 | 3/1989 |
| 6,010,716 | A | 1/2000 | Saunal et al. ............... 424/449 | ES | 2005164 | 3/1989 |
| 6,010,877 | A | 1/2000 | Sathe et al. ............... 435/69.1 | FR | 2792529 | 10/2000 |
| 6,024,974 | A | 2/2000 | Li | GB | 1541710 | 3/1979 |
| 6,024,976 | A | 2/2000 | Miranda et al. ............ 424/449 | GB | 2105589 | 3/1983 |
| 6,063,398 | A | 5/2000 | Gueret | GB | 2232082 | 5/1990 |
| 6,066,292 | A | 5/2000 | Purwar | SU | 1802340 | 3/1993 |
| 6,086,905 | A | 7/2000 | Peck et al. ................ 424/406 | WO | WO 88-08702 | 11/1988 |
| 6,107,318 | A | 8/2000 | Pocchiari et al. ........... 514/366 | WO | WO 89-12445 | 12/1989 |
| 6,149,737 | A | 11/2000 | Hattori et al. .............. 148/403 | WO | WO 90-13294 | 11/1990 |
| 6,218,421 | B1 | 4/2001 | King .......................... 514/421 | WO | WO 93/00313 | 1/1993 |
| 6,221,627 | B1 | 4/2001 | Sathe et al. ............... 435/69.1 | WO | WO 93/07842 | 4/1993 |
| 6,299,900 | B1 | 10/2001 | Reed et al. | WO | WO 93/14727 | 8/1993 |
| 6,300,365 | B1 | 10/2001 | Holman ..................... 514/418 | WO | WO 93/16073 | 8/1993 |
| 6,331,636 | B1 | 12/2001 | Romero et al. ............ 548/235 | WO | WO 93/23035 | 11/1993 |
| 6,514,949 | B1 | 2/2003 | Linden et al. ................ 514/46 | WO | WO 93/23055 | 11/1993 |
| 6,576,649 | B1 | 6/2003 | Kis | WO | WO 94/04109 | 3/1994 |
| 6,620,429 | B1 | 9/2003 | Müller | WO | WO 94-07468 | 4/1994 |
| 6,685,959 | B1 | 2/2004 | Moreau et al. ............. 424/449 | WO | WO 91/21244 | 9/1994 |
| 6,884,434 | B1 | 4/2005 | Muller et al. ............... 424/487 | WO | WO 94-26703 | 11/1994 |
| 7,067,149 | B1 | 6/2006 | Chauveau et al. .......... 424/465 | WO | WO 95/00122 | 1/1995 |
| 7,087,247 | B2 | 8/2006 | Li et al. ..................... 424/499 | WO | WO 95/01767 | 1/1995 |
| 2001/0005377 | A1 | 12/2001 | Brecht | WO | WO 95/05137 | 2/1995 |
| 2002/0010201 | A1 | 1/2002 | Brecht ....................... 514/388 | WO | WO 95/05138 | 2/1995 |
| 2002/0110585 | A1 | 8/2002 | Godbey et al. | WO | WO 96/00110 | 1/1996 |
| 2002/0132827 | A1 | 9/2002 | Nichols et al. ............. 514/311 | WO | WO 96/22083 | 7/1996 |
| 2003/0026830 | A1 | 2/2003 | Lauterback et al. | WO | WO 96/22084 | 7/1996 |
| 2003/0027793 | A1 | 2/2003 | Lauterback et al. | WO | WO 96/31210 | 10/1996 |
| 2003/0032070 | A1 | 2/2003 | Good et al. ................ 435/7.21 | WO | WO 96/40087 | 12/1996 |
| 2003/0124191 | A1 | 7/2003 | Besse et al. ................ 424/489 | WO | WO 97/09971 | 3/1997 |
| 2003/0166709 | A1 | 9/2003 | Rimpler et al. | WO | WO 97-29735 | 8/1997 |
| 2003/0180332 | A1 | 9/2003 | Rimpler et al. | WO | WO 98-00126 | 1/1998 |
| 2004/0009214 | A1 | 1/2004 | Klose et all | WO | WO 98/57651 | 12/1998 |
| 2004/0018241 | A1 | 1/2004 | Houze et al. ............... 424/486 | WO | WO 99/15210 | 4/1999 |
| 2004/0048794 | A1 | 3/2004 | Schollmayer et al. | WO | WO 99-49844 | 10/1999 |
| 2004/0057985 | A1 | 3/2004 | Bracht ....................... 424/449 | WO | WO 99-49852 | 10/1999 |
| 2004/0072986 | A1 | 4/2004 | Li et al. ..................... 528/355 | WO | WO 99/51230 | 10/1999 |
| 2004/0081683 | A1 | 4/2004 | Schacht et al. | WO | WO 99/58190 | 11/1999 |
| 2004/0110673 | A1 | 6/2004 | Steinkasserer et al. ...... 514/414 | WO | WO 00/02053 | 1/2000 |
| 2004/0116537 | A1 | 6/2004 | Li et al. | WO | WO 00/03715 | 1/2000 |
| 2004/0137045 | A1 | 7/2004 | Breitenbach et al. | WO | WO 00/15108 | 3/2000 |
| 2005/0032873 | A1 | 2/2005 | Hatzenbuhler et al. ..... 514/414 | WO | WO 00/24455 | 5/2000 |
| 2005/0033065 | A1 | 2/2005 | Mueller et al. | WO | WO 00/27357 | 5/2000 |
| 2005/0260577 | A1 | 3/2005 | Barrett et al. ............... 713/201 | WO | WO 00/35954 | 6/2000 |
| 2005/0079206 | A1 | 4/2005 | Schacht et al. | WO | WO 00/37426 | 6/2000 |
| 2005/0136101 | A1 | 6/2005 | Berthold .................... 424/448 | WO | WO 00/37438 | 6/2000 |
| 2005/0175678 | A1 | 8/2005 | Breitenbach | WO | WO 01-13902 A2 | 8/2000 |
| 2005/0182090 | A1 | 8/2005 | Mierau et al. .............. 514/304 | WO | WO 01-13903 A2 | 8/2000 |
| 2005/0197385 | A1 | 9/2005 | Scheller et al. | WO | WO 00/64444 | 11/2000 |
| 2005/0260254 | A1 | 11/2005 | Breitenbach et al. ....... 424/449 | WO | WO 01/13899 | 3/2001 |
| 2006/0263419 | A1 | 11/2006 | Wolff | WO | WO 01/38321 | 5/2001 |
| | | | | WO | WO 01/39756 | 6/2001 |
| | | FOREIGN PATENT DOCUMENTS | | WO | WO 01/62249 | 8/2001 |
| CA | | 2 532 859 | 2/2005 | WO | WO 02-15903 A2 | 8/2001 |
| CA | | 2 547 820 | 6/2005 | WO | WO 02-26217 A2 | 9/2001 |
| CA | | 2 546 797 | 7/2005 | WO | WO 01/81343 | 11/2001 |
| CA | | 2 568 850 | 2/2006 | WO | WO 01/87308 | 11/2001 |
| DE | | 1256340 | 12/1967 | WO | WO 01/89453 | 11/2001 |
| DE | | 294 867 | 10/1983 | WO | WO 02-074286 A1 | 3/2002 |
| DE | | 4325855 | 2/1995 | WO | WO 02/38646 | 5/2002 |
| DE | | 198 14 084 | 10/1999 | WO | WO 02/45699 | 6/2002 |
| DE | | 199 40238 | 3/2001 | WO | WO 02-089777 A1 | 11/2002 |
| DE | | 100 60550 | 4/2002 | WO | WO 02/89778 | 11/2002 |
| DE | | 10359528-7 | 12/2003 | WO | WO 02/98367 | 12/2002 |
| DE | | 10361258-0 | 12/2003 | WO | WO 03/012137 | 2/2003 |
| EP | | 0026848 | 9/1980 | WO | WO 03-028725 | 4/2003 |
| EP | | 0168505 | 5/1984 | WO | WO 03/029233 | 4/2003 |
| EP | | 0230629 | 8/1987 | WO | WO 00/38669 | 7/2003 |
| EP | | 0305756 | 3/1989 | WO | WO 03/068207 | 8/2003 |
| EP | | 0334538 | 9/1989 | WO | WO 03/069332 | 8/2003 |
| | | | | WO | WO 03/088958 | 10/2003 |

| | | |
|---|---|---|
| WO | WO 03-088958 A2 | 10/2003 |
| WO | WO 03/092677 | 11/2003 |
| WO | WO 03-092677 A1 | 11/2003 |
| WO | WO 03/105852 | 12/2003 |
| WO | WO 04/000263 | 12/2003 |
| WO | WO 04/012719 | 2/2004 |
| WO | WO 04/012721 | 2/2004 |
| WO | WO 04/012730 | 2/2004 |
| WO | WO 04/039320 | 5/2004 |
| WO | WO 2004-039320 A2 | 5/2004 |
| WO | WO 04/058247 | 7/2004 |
| WO | WO 2005-009424 A1 | 2/2005 |
| WO | WO 2005-009425 A1 | 2/2005 |
| WO | WO 05/042055 | 5/2005 |
| WO | WO 05/058296 | 6/2005 |
| WO | WO 2005-058296 A1 | 6/2005 |
| WO | WO 2005-063236 A1 | 7/2005 |
| WO | WO 2005-063238 A1 | 7/2005 |
| WO | WO 06/015737 | 2/2006 |
| WO | WO 06/050976 | 3/2006 |
| WO | WO 2006-039532 | 4/2006 |
| WO | WO 06/069030 | 6/2006 |

OTHER PUBLICATIONS

Blanchet et al., 2004, "Relevance of the MPTP primate model in the study of dyskinesia priming mechanisms", Parkinson and Related Disorders, vol. 10, pp. 297-304.
Braun et al., 2005, "Steady-State Pharmacokinetics of Rigotine in Patients with Early-Stage parkinson's Disease", EFNS Conference.
Burn, 2000, "(2) Parkinson's Disease Treatment", Neurology, vol. 264, p. 476-479.
Chan et al., 2004, "Parkinson's Disease - current and future aspects of drug treatment", Hospital Pharmacist, vol. 11, p. 18-22.
Chase et al., 1995, "Dopamine-Receptor Subtype-Selective Agonists in the Treatment of Parkinson's Disease", Clinical Neuro. Suppl. 1, p. S207-215.
Chaudhuri, 2002, "The basis for day and night-time control of symptoms of Parkinson's disease", EFNS, ., Euro. J. of Neuro., vol. 9, Suppl. 3p. 40-43.
Chiang C.M. et al., 1995, "A two-phase matrix for the delivery of N-0923, a dopamine agonist", Proc. Int. Symp. Controlled Release Bioact. Mater. 22, p. 710-711.
Danhof et al., 1998, "An Integrated Pharmacokinetic-pharmacodynamic approach to optimization of R-apomorphine delivery in Parkinsons", Adv Drug Deliv Review, p. 253-253.
den Daas et al., 1990, "Transderm admin of dopamine agonist N-0437", Archives of Pharm, p. 655-659.
Deutsche Apotheker Zeitung, 2004, "Arzneimittel und Therapie", Arzneimittel in der Entwicklung, p. 6015 21-6027 33.
Dijkstra et al., 1989, "A Novel and Facile Syntresis of a Series of 5-OH-8-Cl-2 (Alkylamino) Tetralins A Pharmacological Evaluation", Pharmaceutisch Weekblad Scientific ed, p. M5.
Dryer et al., "Biochemical and Behavioral", Analgesics p. 845, Abstract No. 3051.
Foley et al., 2004, "Dopamine receptor agonists in the therapy of Parkinson's Disease", J. Neural Trans., vol. 111, p. 1375-1446.
Freeman et al., 2001, "Ropinirole for Restless Legs Syndrome (RLS): An Open-Label and Double-Blind Placebo-Controlled Study", Neurology, vol. 56, No. 8, Suppl. 3, p. A5, S02.005.
Friedman and Chou, 2004, "Sleep and fatigue in Parkinson's disease", Parkinsonism and Related Disorders, vol. 10, p. S27-S35.
Gerlach et al., 2003, "Arguments for the use of dopamine receptor agonists. . . ", J Neural Trans, Suppl. 65, p. 167-183.
Hacksell et al., 1979, "N-Alkylated 2-Aminotetralins Central Dopamine-Receptor Stimulating Activity", J Medicinal Chemistry, vol. 22, No. 12, p. 1469-1475.
Hagan et al., 1997, "Parkinson's disease: prospects for improved drug therapy", TIPS, vol. 18, p. 156-163.
Hauser and Lyons, 2004, "Future therapies for Parkinson's disease", Neurol. Clin., vol. 22, p. S149-166.

Hundemer et al., 1001, "Safety of Pergolide in the Treatment of Restless Legs SYndrome RLS: Results of . . .", Sleep, vol. 24, Abstr. Suppl. p. A17.
Johnston and Brotchie, 2004, "Drugs in development for Parkinson's disease", Current Opinion in Investigational Drugs, vol. 5, No. 7, p. 720-726.
kehr and Schellter, 2005, "Continuous Delivery of Rotigotine Leads to Continuous . . .", EFNS Conf.
Korczyn and Nussbaum, 2002, "Emerging Therapies in the Pharmacological Treatment of Parkinson's Disease", Drugs, vol. 62, p. 775-786.
Kostowski et al., 1992, "5-Hydroxytryptamine$_{IA}$ Receptor Agonists in Anumal Models of Depression and Anxiety", Pharma & Toxic. vol. 71, p. 24-30.
Kreiss et al., 1995, "Dopamine receptor agonist potencies for inhibition of cell firing correlate with Dopamine $D_3$ receptor binding affinities", European Journal of Pharmacology, vol. 277, p. 209-214.
Kulkami and Verma, 1992, "Pharmacology of Dopamine Receptor Subtypes - An Update", Drugs of Today, vol. 28, p. 201-217.
Lahti et al., 1996, "Affinities and intrinsic activities of dopamine receptor agonists for the $hd_{21}$ and $hD_{4.4}$ receptors", European Journal of Pharm., vol. 301, p. R11-R13.
Levien, 2005, "Summary of New Drug Applications and Biologic License Applications Submitted to Food and Drug Administration", Advances in Pharm. vol. 3(1) p.62-92.
LeWitt et al., 2005, "Rotigotine Transdermal System in Treatment of Patients with Advvanced-Stage Parkingon's Disease", EFNS Conference.
Li et al., 2000, "Optimization of Transdermal Iontophoretic Delivery of Apomorphine . . . ", Proceed Intl Symp Control Rel Bioact Mater, p. 952-953.
Li et al., 2001, "Iontophoretic Delivery of Apomorphine In Vitro: Physicochemic Considerations", Pharm Research, vol. 18(11) p. 1509-1513.
Linazasoro, 2004, "Recent Failures of New Potential Symptomatic Treatments for Parkinson's Disease-Causes and Solutions", Movement Disorders, vol. 19, p. 743-754.
Loschmann et al., 1989, "Stereoselective reversal of MPTP-induced parkinsonism in the Marmoset after dermal application of N-0437", European Jrnl Pharm., vol. 166, p. 373-380.
Luzardo et al., 2001, "Iontophoretic Delivery of Ropinirole Hydrochloride: Effect of Current Density and Vehicle Formulation", Pharm Research, vol. 18(12), p. 1714-1720.
Mackonochie, 2003, "Drug Discovery Technology 2003-Seventh Annual Conference and Exhibition Science, business and IT for drug discovery II", Drugs, vol. 6, p. 420-422.
Metman et al., 2001, "Continuous Transdermal Dopaminergic Stimulation in Advanced Parkinson's Disease", Clinical Neuropharm, vol. 24(3) p. 163-169.
Mouradian and Chase, 1989, "Parkinson's disease: therapeutic aspects", Current Opinion in Neurology and Neuroserg, vol. 2, p. 309-313.
Neophytides et al., 1982, "The ose of lisuride, a potent dopamine and serotonin agonist, in the treatment of progressive supranuclear palsy", J. of Neurology, Neurosurgery, Psychiatry, vol. 45, p. 261-263.
Park et al., 1972, "Evaluation of an Aminotetraline, CP 14.368, as an Antidepressant", Cur. Thera. Res., vol. 14(2) p. 65-70.
Pascual et al., 1992, "Dopamine D1 and D2 Receptors in Progressive Supranuclear Palsy: An Autoradiographic Study", Annals of Neurology, vol. 32(5) p. 703-707.
Pierot et al., 1988, "D1 and D2 dopamine type receptors in patients with Parkinson's disease and progressive supranuclear palsy", J. of Neurological Sciences, vol. 86, p. 291-306.
Prous-ed, 2004, "Annual Update 2003/2004 -- Treatment of Neurological Disorders", Drugs, vol. 29(3), pp. 253-261.
Riederer et al., 2000, "Workshop II - Neuroprotection - the Lugano consensus", J Neurol., vol. 247[Suppl.4], p. IV/36—IV/37.
Roy et al., 1990, "Transdermal Delivery of Narcotic Analgesics:pH, Anatomical and Subject Influences on . . . ", Pharm Research, vol. 7(8), p. 842-847.

Roy et al., 1996, "Controlled Transdermal Delivery of Fentanyl: Characterizations of P ressure-Sensitive . . . ", J Pharm Sci., vol. 85(5), p. 491-495.
Scheller et al., 2005, "Continuous Administration of Rotigotine", EFNS Conference.
Scriabine, 2003, "CNS Forum - Advancements in Clinical Trials and Drug Development", CNS Drug Reviews, vol. 9(4), p. 389-395.
Silber et al., 2001, "Pramipexole in the Management of Restless Legs Syndrome: An Extended Study", Sleep, vol. 24, p. A18.
Sonesson and Boije, 1993, "Orally Active Central Dopamine and Serotonin Receptor Ligands: 5-,6-,7-, and 8-. . . ", J Med Chem., vol. 36, p. 3409-3416.
Sonesson, et al., 1995, "Synthesis and Evaluation of Pharmacological and Pharmacokinetic Properties. . . ", J. Med. Chem., vol. 38, p. 1319-29.
"SR 58611A", 2003, Drugs R&D, 4;6, p. 380-382.
Stiasny-Kolster et al., 2005, "Rotigotine in the Treatment of Moderate to Severe Idiopathis Restless Legs Syndrome. . . ", EFNS Conf.
Stichel and Scheller, 2005, "Rotigotine Prevents Neurodegeneration in a Mouse Model of Parkinson's Disease", EFNS Conference.
Strange, 1993, "New Insights into Dopamine Receptors in the Central Nervous System", Neurochem. Intl., vol. 22, p. 223-236.
Timmerman et al., 1989, "Microdialysis and striatal dopamine release: stereoselective actions of the enantiomers of N-0437", European Jrnl of Pharm., vol. 162, p. 143-150.
Timmerman et al., 1990, "The potential antipsychotic avtivity of the partial dopamine receptor agonist (+)N-0437", European Jrnl Pharm., vol. 186, p. 253-260.
Timmerman, 1993, "Dopaminergic receptor agents and the basal ganglia: pharmacological properties and interactions with the GABA-ergic system", Pharmacy World and Science, vol. 15, p. 90-92.
Tuite and Riss, 2003, "Recent Developments in the Pharmacological Treatment of Parkinson's Disease", Expert Opin. Investig. Drugs, vol. 12, (8), p. 1335-1352.
van der Geest et al., 1997, "Iontophoretic Delivery of Apomorphine 1: *In Vitro* Optimization and Validation", Pharm Research, vol. 14, p. 1798-1803.
van der Geest et al., 1998, "Validation and testing of new iontophoretic continuous flow through transport cell", J of Controlled Release, vol. 51, p. 85-91.
Waters, 2005, "Other Pharmacological Treatments for Motor Complications and Dyskinesias", Movement Disorders, vol. 20, Suppl. 11, p. S38-S44.
Welner et al., 1989, "Autoradiographic Quantification of Serotonin $1_A$ Receptors in Rat Brain. . . ", Synapse, vol. 4, p. 347-352.
Wikstrom et al., 1985, "Resolved Monophenolic 2-Aminotetralins and 1,2,3,4,4a,5,6,10b- Octahydrobenzo[f]quinolines: Structural and Stereochemical Considerations. . . ", J Med Chem. vol. 28, p. 215-225.
Wikstrom, 1992, "5 Centrally Acting Dopamine D2 Receptor Ligands: Agonists", Progress in Medicinal Chemistry, vol. 29, p. 185-210.
Zhdanova, 2004, "Advances in the management of insomnia", Expert Opin. Pharmacother, vol. 5, p. 1573-1579.
Zucconi et al., 2001, "Effectiveness of the D2-Agonist Cabergoline as Single-Drug Therapy. . . ", Sleep, vol. 24, Abs Suppl., p. A19, Abstract No. 030 N.
AADAC (2004) Alberta Alcohol and Drug Abuse Commission; www.aadac/.com.
Abbas (1999) Hum. Mol. Genet 8, 567.
Alekov et al. (2000) J. Physiology 529(3), 533-539.
Amt (1984) Pol. J. Pharmacool. Pharm. 36, 221-230.
Balsara et al. (1982) Ind. J. Physiol. Pharmac 26(3), 183-195.
Barfnecht et al. (1973) J. Medicinal Chemistry 16(7), 804-805.
Barzilai (2001) Cell Mol. Neurobiol. 21(3), 215-235.
Beaulieu (1984) Eur. J. Pharmacool. 105, 15-21.
Becker (2002) J. Neurol. 249(Suppl. 3) III/40-III/48.
Bell (1977) Br. J. Pharm. 61, 291-295.
Bijak (1988) Eur. J. Pharmacol. 149, 41-47.
Bischoff et al., (1986) Satellite Symposia IUPHAR 9th Int. Cong. Pharmacol., 397-398.

Borsini (1988) Eur. J. Pharmacol. 148, 301-307.
Bunney et al. (1982) Pharmacopsychiatry 15, 111-115.
Cliendo et al. (2005) Current Medicinal Chemistry 12, 171-173.
Camicioli (2002) R. Drugs Today (Barc) 38(10), 677-686.
Carp et al. (1982) Brain Research 242, 247-254.
Chandler et al. (1990) Neuroscience 38(2), 437-445.
Chiodo et al. (1980) Eur. J. Pharmacol. 64, 203-204.
CHristie et al. (1982) Brit. J. Psychiatry 140, 268-273.
Collado-Seidel et al. (1999) CNS Drugs 12(1) 9-20.
Corsini et al. (1981) Biological Psychiatry, 742-745.
Dawson (2002) Nature Neuroscience Supplement 5, 1058-1061.
De Boer et al. (1998) Neuropharmacology 27(4), 399-408.
De Ceballos et al. (1985) Eur. J. Pharmacology 116, 257-262.
DeNinno et al. (2001) J. Organic Chemistry 66, 6988-6993.
Deakin (2002) Int. Clin. Psychopharm. 17(Suppl. 1), S13-S24.
Den Daas (1990) Naunyn-Schmiedeberg's Archives of Pharmacology 341, 186-191.
Den Daas (1991) J. Pharm. Pharmacology 43, 11-16.
Seutsche Apotheker Zeitung (2004) Arzneimittel in der Entwicklung, 144(52), 21-33.
Diggory et al. (1984) Eur. J. Pharmacol. 105, 257-263.
Doggett (1973) Neuropharmacology 12, 213-220.
Domino et al. (1993)J. Pharmacol. Exp. Therap. 264(1), 221-225.
Duarte (1995) J. Pharmacy Technology 11, 226-228.
Duterte-Boucher et al. (1998) Eur. J. Pharmacol. 154, 185-190.
EMEA (2005) pp. 1-9, http://www.emea.eu.int/humandocs/PDFs/EPAR/Sifrol/059197EN6.pdf.
Eberhardt (2003) Toxicology Letter 139(2), 135-151.
Errico et al. (2001) Neuroscience 102(2), 361-367.
Estrada-Camerena et al. (2006) Neropsychopharmacology 31, 247-255.
Faedda et al. (1989) Biochemical Pharmacology 38(3), 473-480.
Fajardo et al. (2003) Int. Immunopharm. 3, 1345-1352.
Gerlach (2003) Neurotox. Res. 5(1), 43-51.
Gnegy et al. (1980) Neuropharm. 19, 319-323.
Goldenberg et al. (2004) J. Amer. Med. Assoc. 292(19), 2388, 2395.
Goodwin et al. (1987) Psychopharmacology 91, 500-505.
Gorman (1999) J. Clinical Psychiatry 60(Suppl. 17), 9-13.
Graeff et al. (1971) Arch. Int. Pharmcodyn. 193, 134-148.
Green et al. (1983) Br. J. Pharmacol. 80, 377-385.
Grippo et al. (2005) Psychopharmacology 179, 769-780.
Gstimer (1963) Pharmaz. Industrie 25, 503.
Guldenpfennig (2005) Clinical Neuropharmacol. 28, 106-110.
Guttman (2003) Canadian Med. Assoc. Journal 168(3), 293-301.
Gyure et al. (1985) Proc. 4th Congress Hungary Pharmacol. Soc. Budapest 2, 309-312.
Hackling (2002) ChemBioChem 3, 947-961.
Haddjeri et al. (1999) Biol. Psychiatry 45, 1163-1169.
Happe (2004) CNS Drugs 18(1), 27-36.
Henderson (2003) J. Neurol. Neurosurg. Psychiatry 74, 956.
Hirsch (2003) Ann NY Academy Science 991, 214-228.
Hobson (2003) Can. J. Neurol. Sci. 30(Suppl. 1) S2-S9.
Holcomb et al. (1982) Eur. J. Pharmacol. 82, 173-178.
Holman (2004) Arthritis & Rheumatism 50(Suppl. 9), S698.
Holman (2004) J. Musculoskeletal Pain 12(1), 69-74.
Holman (2005) Arthritis & Rheumatism 52(8), 2495-2505.
Holmberg et al. (2004) J. Med. Chem. 47, 3927-3930.
Hornykiewicz (2002) Encyclopedia of Life Science vol. 13, 695-704.
Hsu and Roos (1992) Cygnus Therapeutic Systems Project Report N-0923, 2-19.
Hughes (1992) J. Neurol. Neurosurg. Psychiatry 55, 181-184
Hutchinson et al. (1999) J. Neurol. Neurosurg. Phychiatry 67, 815-818.
Jackson (1989) Naunyn-Schmiedeberg's 340, 355-365.
Jimmerson et al. (1976) J. Pharm. Pharmacol. 28, 845.
Johnson et al. (1970) Western Pharma. Society 13, 87-92.
Johnson et al. (1970) Life Science 9(1), 471-476.
Joyce (2001) Pharmacol. & Ther. 90, 231-259.
Kamata (1984) Life Sciences 34, 2419-2427.
Keller (1980) Adv. Biochem. Psychopharmacol. 24, 175-179.
Kelly (1997) Pharmacology Therapeutics 74(3), 299-316.
Khaitan (1994) Psychopharmacol. 113, 529-542.

Kim et al. (1993) J. Pharmaceutical Sciences 82(4), 355-361.
Kitada (1998) Nature 392, 605-608.
Klimek et al. (1987) Eur. J. Pharmacol. 139, 163-169.
Klimek et al. (1989) J. Pharm. Pharmacol. 41, 455-558.
Knott et al (1990) GABA 336-346.
Koe et al. (2006) Science Finder Scholar, Sep. 22, p. 2.
Koide et al. (1981) Life Sciences 28(10), 1139-1145.
Krygowska-Wajs (2000) Funct. Neurol. 15, 41.
Lee et al. (1982) Psychiatry Research 7, 111-119.
Lev (2003) Prog. Neuropsychopharm. Biol. Psychiatry 27(2), 245.
Littlejohn (2006) Current Pharm. Design 12, 3-9.
Liu et al. (1993) J. Med. Chemistry 36, 4221-4229.
Lucking (2000) N. Engl. J. Med. 342, 1560-1567.
March (1985) Advanced Organic Chemistry: John Wiley & Sons, 3rd Ed., pp. 16-18.
Mark (2001) Neurol. Clin. 19(3), 607-627.
Matsumine (1997) Am. J. Genet. 60, 588.
McCain (1994) in Wall & Melzack, eds. Textbook of Pain: Churchill Livingstone, pp. 475-493.
Menon et al. (1972) Eur. J. Pharmacol. 19, 43-51.
Merkus (1999) Advanced Drug Delivery Reviews 36, 41-57.
Michel et al. (2002) Rev. Neurol. (Paris) 158(1), 7S24-7S32.
Modigh et al. (1984) Neurotransmitter & Receptor Machanisms, pp. 18-27.
Mucke (2003) IDrugs 6(9), 894-899.
Mulroney et al. (1994) J. Pharmacol. & Experimental Therapies 288(2), 862-867.
Muramatsu et al. (2003) GLIA 42, 307-313.
Murray (1997) The Lancet 349, 1498-1504.
Nampiaparampil et al. (2004) American J. Managed Care 10(11 Pt. 1), 794-800.
Newman-Tancredi et al. (2002) J Pharmacol. Exp. Therap. 303(2), 805-814.
Nowak et al. (1985) J. Neurol. Transmission 64, 227-238.
Nurse et al. (1984) Neurochemical Research 9(9), 1231-1238.
Nussbaum (2003) N. Engl. J. Medicine 348(14), 1356-1364.
Ong et al. (1988) J. Pharm. Pharmacol. 40, 746-747.
Ono et al. (1984) Neuropharmacol. 23(6), 637-642.
Ono et al. (1989) J. Pharmacobiol-Dyn. 12, 383-391.
Ostow (2002) American J. Psychiatry 159(2), 320-321.
Page (2002) J. Pharmacol. Exp. Therap. 302(3), 1220-1227.
Pankratz (2003) Am. J. Hum. Genet. 72, 1053-1057.
Park (2002) Drug Delivery Technology 2(5), http://www.drugdeliverytech.com/cgi-bin/issues.cgi?idIssue=6 and http://www.drugdeliverytech.com/cgi-bin/articles.cgi?idArticle=60.
Parkinson Study Group (2003) Arch. Neurol. 60(12), 1721-1728.
Pessoa-Mahna et al. (2003) Mini Reviews in Medicinal Chemistry 3(2), 77-93.
Pfister (1998) Drug and Cosmetic Industry Oct.
Pfister (1999) Pharm. Tech., Mar. 126-138.
Pfister and Hsieh (1990) Pharm. Tech. Sep., 132-140.
Pfister and Hsieh (1990) Pharm. Tech. Oct., 54-60.
Pfister et al. (1991) Chemistry in Britain Jan., 43-46.
Pfister et al. (1992) Pharm. Tech. Jan., 42-58 and 83.
Piercey et al. (1990) Eur. J. Pharmacol. 192, 219-226.
Polymeropoulos (1997) Science 276, 2045-2047.
Porsolt (1979) Biomedicine 30, 139-140.
Pradhan et al. (1989) Drug Develop. Research 18, 113-118.
Prunier (2003) NeuroImage 19, 810-816.
Pulvirenti (2002) TRends Pharmacol. Sci. 23(4), 151-153.
Rammsayer (1997) Int. J. Neurosci. 91, 45.
Reith (1986) Pharmcol. Biochem. & Behavior 24, 305-307.
Robertson (1981) Neuropharmacology 20, 1335-1336.

Saleh et al. (1989) Peptides 10, 35-39.
Sarges et al. (1973) J. Medicinal Chemistry 16(9), 1003-1011.
Schäfers (2003) Pain 104, 579-588.
Schatzberg (2002) Human Psychopharmacol. 17, S17-S22.
Schelkunov (1980) J. Neurol. Transmission 47, 307-312.
Scheller et al. (2005) EFNS Conference, "Continuous Administration of Rotigotine Does Not Induce Dyskinesia in a Rat Model of Parkinson's Disease".
Seiler (1986) J. Med. Chem. 29, 912-917.
Serra et al. (1981) Apomorphine & Other Dopaminomimetics 1, 133-142.
Serra et al. (1981) Eur. J. Pharmacol. 72, 131-135.
Serra et al. (1980) Pharm. Res. Comm. 12(6), 619-624.
Sharma (2002) Neurol. Clin. N. Am. 20, 759-778.
Shepperson et al. (1982) Eur. J. Pharmacol. 81, 627-635.
Sherman (1982) Pharmacology Biochemistry & Behavior 16, 449-454.
Shiro et al. (1996) Psychiatry & Clinical Neurosciences 50, 141-146.
Skuza et al. (1989) Pol. J. Pharmacol. Pharm. 41, 421-429.
Sokoloff (1990) Nature 347, 146-151.
Spampananto et al. (2001) J. Neuroscience, 21(19), 7481-7490.
Stern (2004) Annals of Neurology 56(2), 169-170.
Stiasny-Kolster et al. (2000) Sleep 23(3), 1-6.
Stiasny Kolster et al. (2005) EFNS Conference, "Rotigotine in the Treatment of Moderate to Severe Idiopathic Restless Legs Syndrome-a Double-Blind Placebo-Controlled Multi-Center Dose-Finding Study".
Stichel et al. (2005) EFNS Conference, "Rotigotine Prevents Neurodegeneration in a Mouse Model of Parkinson's Disease".
Stockmeier et al. (1992) Neuropharmacol. 31(11), 1089-1094.
Stockmeier et al. (1997) Neuropsychopharmacology 16(2), 162-173.
Stockmeier (1998) J. Neuroscience 18(18), 7934-7401.
Sumiyoshi et al. (1997) Neuropsychopharmacol. 16, 183-190.
Swart (1992) International Journal of Pharmaceutics 88, 165-170.
Swart (1993) Toxicology Methods 3, 279, 289 last paragraph.
Swart (1994) J. Analytical Toxicology 18, 71-77.
Swart (1995) Pharmaceutical Sciences 1, 437-440.
Tassin (1998) Am. J. Hum. Genet. 63, 88-94.
Thomas and Pfister (1991) S.T.P. Pharma Sciences 1(1), 38-46.
Thomas (1999) J. Neurol. Neurosurg. Psychiatry 67, 277-279.
Timmerman et al. (1989) Pharmaceutisch Weekblad Scientific, M5.
Troutman et al. (2003) Pharmaceutical Research 20(8), 1192-1199; 1200-1209; 1210-1224.
Valente (2001) Am. J. Hum. Genet. 68, 895.
van de Donk (1980) Rhinology 18, 93-104.
Van Dujin (2001) Am. J. Hum. Genet. 69, 629-634.
van Gaalen et al. (2002) Genes, Brain & Behavior 1, 174-177.
Van Laar (1992) Ned. Tijdschr. Geneeskd. 136(14), 702-704.
van Riezen (1977) BRitish J. Pharmacology 60, 521-528.
Van Vliet (1996) J. Med. Chem. 39, 4233-4237.
Vanacore (2002) Neurol. Sci. 23, S119.
Vance (1983) Research Comm. In Chem. Pathology & Pharmacology 40(2), 345-348.
Vila (2003) Nat. Rev. Neurosci 4(5), 365.
Wenning et al. (2004) Lancet Neurology 3, 93-103.
Westenberg (1999) J. Clin. Psychiatry 60(Suppl. 17), 4-8.
Wilner et al. (1988) Progress in Catecholamine Research, Part C, Clinical Aspects, 275-279.

* cited by examiner

INJECTABLE PHARMACEUTICAL COMPOSITION FOR SYSTEMATIC ADMINISTRATION OF PHARMACOLOGICALLY ACTIVE INGREDIENTS

This application is a 371 of PCT/EP01/09596 filed Aug. 21, 2001 and claims priority to German Application No. 10041478.8 filed Aug. 24, 2000.

BRIEF DESCRIPTIONS OF THE INVENTION

This invention relates to novel pharmaceutical compositions for the systemic administration of pharmacologically active agents.

In particular the invention relates to an injectable pharmaceutical composition comprising
  (a) a pharmacologically active agent in its solid phase
  (b) a vehicle essentially consisting of polyol fatty-acid esters with an esterification level of over 80%
  (c) a wetting agent essentially consisting of polyol fatty-acid esters with a monoester component of over 60%.

TECHNICAL BACKGROUND

Many biologically active substances such as certain low-molecular pharmaceutical agents, peptides, nucleic acids, vaccines or hormones are preferably administered in parenteral fashion.

The reason in many cases is a strong mechanical, chemical or enzymatic degradation in the stomach, intestines or liver of patients after oral administration, or limited bioavailability due to inadequate resorption from the gastrointestinal tract.

One example of a strongly degradation-prone agent is N-0923 (S(-)-2-(N-propyl-N-2-thienylerhyl-amino)-5-hyroxytetralin), a dopamine D2 agonist for treating Parkinson's disease. Because of a distinct first-pass effect the bioavailability after oral administration is as low as about 0.5% (Swart and Zeeuw, Pharmazie 47 (1992), ruling out oral forms of N-0923 administration.

Other examples of agents with inadequate gastrointestinal absorption include peptides, proteins, enzymes or nucleic acids which when administered orally are usually not absorbed or only to a therapeutically irrelevant extent.

There is a substantial demand for these active agents in the form of parentally applicable medications. Yet many agents have a short half-time value even when injected since they are rapidly eliminated from the body.

Here again, N-0923 is a good example. In tests with animals, the half-time value of intravenously injected aqueous N-0923 solutions was 52 minutes (Walters et al, J Pharmac Sci 83 (1994) 758), and after subcutaneous administration it was 60–70 minutes (Belluzzi, Movement Disorders, 9.2 (1994) 147), which in the case of an extended therapy would require administration at a frequency altogether unacceptable to the patient.

It is the elimination half-time value especially of many peptides and enzymes that is very limited. For example, insulin injected in an aqueous solution has a half-time value of about 6 minutes, proinsulin C-peptide about 30 minutes.

The situation is similar with the pharmacokinetics of nucleic acids, oligonucleotides or nucleoside analogues. For example, the 5-fluorouracil used in cancer treatment has a half-time value of only 10–20 minutes, it is ineffective when taken orally and it must be administered by continuous infusion.

Consequently, for substances of this type with low oral bioavailability and rapid elimination there is a great demand for systemic medications that significantly reduce the frequency or duration of the therapeutic administration.

One method of retarding injected agents involves the administration in the form of suspensions. When substances are suspended in aqueous solutions, the active agent is precipitated for instance with metal ions or charged substances, with the agent reversibly bound to the ion.

Examples thereof include aqueous zinc-insulin or zinc-insulin-protamine suspensions that have been in use since the 1930s. The ratio between bound and free agent components determines the retention effect to be expected. One example of an insulin-zinc crystal suspension of this type is described in EP-A-0 025 868.

However, developing depot-type medicines of that nature is a difficult matter and depends largely on the characteristics and individual physiochemical properties of the agent concerned. It follows that the results obtained with an agent such as insulin are not or at least not easily reproducible with other agents.

Oily suspensions of aqueous agents have also been around for some time. Their drawback, however, is that the suspensions are viscous to a point where they either would not flow through standard cannulas or they are unstable, so that even after brief storage they form sedimentations from which the suspensions can no longer be fully extracted.

One example for producing stable, injectable oily peptide preparations is described in OS DE 2,306.075. As a first step, the peptides are mixed with a fatty acid aluminum salt and the resulting adsorbate is suspended in oil or the peptides are suspended in an oily gel that contains fatty acid aluminum salt as the gel-forming agent. The drawback of the formulation described, however, is that the aluminum contained therein is a toxic metal which, especially in the case of repeated administration, can create a major problem from the toxicology point of view. Moreover, the release of active agents from gels is difficult to control, the application is often unpleasant for the patient and in the event of incorrect injections there is a significant risk of systemic side effects.

U.S. Pat. No. 5,013,713 describes injectable peptide preparations. For retardation it proposes the conversion of the peptides into low-solubility salts which are then to be suspended in an oily vehicle. This is preferably followed by the addition of dehydrating reagents such as magnesium stearate or fatty acid metal salts that lead to gel formation. The drawback of that method lies in the fact that the pharmacokinetic and pharmacologic properties of the metal salts concerned are difficult to predict. Moreover, the solid particles in the proposed pharmaceutical formulations tend to be subject to aggregation, sedimentation and the formation of insoluble deposits.

This invention was therefore aimed at providing a pharmaceutical formulation that is stable, consists of as few components as possible and is capable of serving as an injectable depository vehicle for a large variety of active agents.

The formulation had to continuously release the active agents over a time span of at least 12 and preferably more than 24 hours, it had to have an adequate shelf life and it had to be highly biocompatible, nontoxic, completely biodegradable and easy to produce.

According to the invention, this objective has been achieved by means of an injectable pharmaceutical formulation comprising a pharmacologically active agent in its solid phase, a liquid vehicle essentially consisting of polyol fatty acid esters with a high esterification level and a wetting agent essentially consisting of polyol fatty acid esters predominantly in the form of monoesters.

Surprisingly, it is possible with this very simple pharmaceutical formulation to obtain a therapeutically meaningful pharmacon plasma level over as many as 48 hours. Yet the composition per this invention is astonishingly simple, cost-effective in its production, stable when stored, thermally sterilizable and easily resuspended.

As another particular advantage, the above-mentioned composition contains very few, well-defined, well-tolerated and biodegradable additives.

Another advantage of this invention is its suitability for a wide range of applications. The pharmaceutical preparation according to the invention lends itself to the administration of numerous different active agents. Individualized selection of the injection volume, the application intervals and the pharmacon concentration of the formulations per the invention permits the easy adaptation of the dosage to the requirements, symptoms and condition of each patient.

Compared to slow-acting substances deposited in the body for releasing pharmacons i.e. active agents over 1, 3 or even 6 months, the pharmaceutical preparations according to the invention offer the advantage of better controllability. For example, with some patients it is desirable to see the biocatalyst removed from the body over a specific time. This is important especially in the case therapeutics with a narrow therapeutic index.

BRIEF DESCRIPTION OF THE DRAWINGS

FIG. 1A and FIG. 1B show N-0923 plasma concentrations in a rat after the subcutaneous administration of four different doses of N-0923 in an oily crystalline suspension. The preparation was administered every 48 hours over several weeks. FIG. 1A shows measured values averaged after the $2^{nd}$ application, FIG. 1B shows measured values averaged after the $46^{th}$ application.

DESCRIPTION OF THE INVENTION

This invention relates to pharmaceutical compositions comprising
(a) at least one pharmacologically active agent/pharmacon in its solid phase
(b) a vehicle essentially consisting of polyol fatty-acid esters with an esterification level of over 80% and preferably higher than 90%, and
(c) a wetting agent essentially consisting of polyol fatty-acid esters with a monoester component of over 60% and preferably higher than 90%.

For the purpose of this patent application, the term "solid phase" refers to the active agent/pharmacon in the form of solid particles, be it free crystals or amorphous particles or even particles bound to a suitable carrier substance. Preference is given to free pharmacon crystals or amorphous pharmacon particles. Especially preferred are free pharmacon crystals containing the active agents in the form of salts.

For the purpose of this patent application, the expression "essentially" means over 90%.

For the purpose of this patent application, the term "vehicle" refers to a continuous phase, liquid at room temperature, in which the solid phase is suspended.

According to the invention, the vehicle consists of a minimum of 90% polyol fatty acid esters with an esterification level of more than 80% but possibly containing up to 10%, preferably less than 5% and most desirably less than 3% of other, additive components such as vegetable oils or fatty acids.

For the purpose of this patent application, the term "polyol fatty acid ester" also encompasses mixtures of various polyol fatty acid esters.

For the purpose of this patent application, the term "wetting agent" refers to a substance that reduces the interfacial tension between the vehicle surface and the pharmacon surface.

According to the invention, the welting agent consists at least up to 90% of polyol fatty acid esters with a monoester content of at least 60% and preferably at least 90%. According to the invention, the wetting agent may contain up to 10%, preferably less than 5% and most desirably less than 3% of additive components such as polyol alcohol condensates.

The pharmaceutical compositions according to the invention are suitable for parenteral or nasal administration.

In particular, the formulations according to the invention lend themselves to being administered by injection, whether by means of conventional syringes or by needle-less injection systems. Examples of such needle-less injection systems are described in U.S. Pat. Nos. 5,840,062 and 4,913,699. The injection can be performed in the traditional mode for depository applications by subcutaneous, intracutaneous, intramuscular or intracranial or intraventricular administration.

Particular preference is given to subcutaneous or intramuscular administration.

Since the ratio between the active agent dissolved in the formulation and the undissolved active agent is a determining factor in the retardation effect as well as in the stability of the formulation, the invention targets especially those compositions that contain active agents/pharmacons which are largely insoluble in the pharmaceutical composition.

The expression "largely insoluble in the pharmaceutical composition" means that less than 10% of the pharmacologically active substance is present in the pharmaceutical formulation in a dissolved state.

Preference is given to pharmaceutical formulations in which less than 5% and ideally less than 3% of the pharmacologically active agent is present in the dissolved state.

Therefore, one preferred object of this invention includes anhydrous pharmaceutical compositions.

The term "anhydrous" in this case refers to a water content of less than 3% and preferably less than 1%.

The invention also relates to pharmaceutical compositions that comprise a pharmacologically active agent in its solid phase, a vehicle essentially composed of polyol fatty acid esters and a wetting agent essentially composed of polyol fatty acid monoesters, which pharmaceutical composition is further characterized in that it is depository i.e. in depot form, releasing said active agent or pharmacon in therapeutically effective quantities over a period of at least 12 hours, preferably at least 24 or 36 hours and most desirably at least 48 hours.

As a benefit thus derived, the frequency of administration of the active agent may be reduced to one application per day or perhaps one administration every two or three days.

Also preferred are implementations of the pharmaceutical formulations according to the invention whose active-agent content is eliminated from the depot in the patient's body after not more than 7 days. After 7 days the amount of the active agent remaining in the body in depot form preferably does not exceed 5% and is ideally less than 1%.

In contrast to slow-acting depots designed to release the pharmacologically active substance over a number of weeks after application in the patient, the compositions according to the invention thus offer the advantage of better controllability: the active agent can be replenished and flushed out as needed over a more focussed time period.

The continuous phase of the compositions according to the invention preferably consists essentially of polyol fatty acid esters whose polyol (polyhydric alcohol) components are in the form of polyols with two to four C-atoms and a variable number of hydroxy groups. Examples thereof include 1,3-propanediol, glycerol, 1,2,3-butanetriol, 1,2,4-butanetriol or 1,3-butanediol.

Glycerol, 1,3-propanediol and 1,3-butanediol are especially well-suited.

According to the invention the overall degree of esterification of the polyols contained in the vehicle is 80–100% and preferably 90–100%.

By appropriate selection of the chain length and the number of double bonds of the fatty acid in the vehicle it is possible in particularly simple fashion to obtain the desired physiochemical properties of the formulation (such as its viscosity).

Preferred forms of implementation according to the invention include pharmaceutical compositions whose vehicle essentially consists of polyol fatty acid esters that contain fatty acids with a chain length of between 6 and 22 C-atoms, preferably between 6 and 14 C-atoms and most desirably between 8 and 10 C-atoms.

The vehicle is preferably composed of polyol fatty acid esters containing over 60% and ideally over 90% saturated fatty acids.

Particular preference is given to medium-chain triglycerides (MCTs) primarily containing saturated fatty acids with chain lengths of 8–10 C-atoms, as described in the pharmacopoeias.

Therefore, in a particularly preferred form of implementation of the invention, the vehicle consists essentially of MCTs.

MCTs are well-defined substances that have proved effective as systemic forms of administration. MCTs offer the advantage of being biodegradable, they are non-irritant and they have excellent physiochemical properties for use in injectable medications as well. MCTs are therefore particularly suitable vehicles for the pharmaceutical preparations according to the invention.

One example is the commercially available triglyceride-caprylic acid/capric acid ester marketed under the tradename Miglycol 812® (by Condea).

The proportion of the continuous phase (of the vehicle) in the pharmaceutical composition is essentially determined by the respective concentration of the active agent, the wetting agent and any other adjuvants. It is usually more than 70% and preferably 88–99.8%, with a particularly suitable concentration being 94–99%.

Another component of the pharmaceutical composition according to the invention consists of at least one wetting agent. These wetting agents perform the important function of reducing the interfacial tension between the surface of the vehicle and the surface of the active agent, thus avoiding an aggregation of the solid particles. At the same time, the addition of a wetting agent serves to control the viscosity of the pharmaceutical composition and the sedimentation pattern.

The pharmaceutical compositions according to the invention contain as their wetting agent primarily polyol fatty acid esters whose monoester component is greater than 60% and preferably greater than 90%.

In a preferred form of implementation the wetting agent consists essentially of fatty acid esters of polyols with two to six C-atoms, such as glycerol, 1,3-butanediol, 1,3-propanediol, 1,2,3-butanetriol, 1,2,4-butanetriol, isopropanol, sucrose or sorbitan.

The preferred wetting agent consists of fatty acid esters of glycerol or 1,2,3-butatriol.

The chain length of the fatty acids in the polyol-fatty acid-monoesters of the wetting agent is preferably 6 to 22 C-atoms and most desirably 6 to 14 C-atoms.

Said polyol-fatty acid-monoesters preferably contain over 60% and ideally over 90% saturated fatty acids.

In another preferred form of implementation of the invention, the wetting agent essentially consists of polyol fatty acid esters containing glycerol or 1,2,3-butanetriol estered with saturated fatty acids having 6–14 C-atoms.

Particular preference is given to commercial products described in pharmacopoeias, such as glycerol monolaurate marketed for instance under the tradename Imwitor 312®, or glycerol monocaprylate marketed under the tradename Imwitor 308® (by Condea).

Glycerol monolaurate is a well-documented substance approved in Germany as a food additive and found to be particularly well-suited to being used in the depot-type preparations according to the invention.

Therefore, in a particularly preferred form of implementation of the invention, the wetting agent essentially consists of glycerol monolaurate and/or glycerol caprylate.

In another preferred form of implementation the pharmaceutical composition is devoid of any phosphatides. This inventor was surprised to find that adding lecithin, described in the literature as a wetting agent, cancels the retardation effect of the composition per this invention. Therefore, as one aspect of the invention, a pharmaceutical composition hereunder is free of any lecithin.

The concentration range of the wetting agent is adapted to the amount of the active agent. The concentration of the wetting agent must be high enough to ensure the wetting of the pharmacon particles. This is easily determined by appropriate tests with which those skilled in the art are familiar. On the other hand, care must be taken to keep the concentration of the selected wetting agent below the crystallization level.

A possible concentration range (in w/w) for the wetting agent is 0.02–10%, preferably 0.1–5% and ideally 0.5–2.5% in each case with appropriate adaptation of the concentration of the wetting agent to the amount of the active agent and to the solubility characteristics of the wetting agent.

Where necessary, the suspension according to the invention may contain additional adjuvants with which pharmacologists are familiar. For example, it may be desirable to add lipid-soluble antioxidants such as vitamin E whenever the vehicle and/or the wetting agent contain(s) unsaturated fatty acids. The pharmaceutical composition may also contain thickeners.

Basically suitable as pharmacologically active substances, pharmacons or biocatalysts are all those agents and their pharmaceutically acceptable salts that retain their solid phase at room temperature and display no or only minor solubility in aliphatic solvents, especially in triglycerides, thus remaining largely insoluble in the pharmaceutical formulation according to the invention. Those skilled in the art are familiar with examples thereof which are also described in major pharmacopoeias.

The term "pharmaceutically acceptable active-agent salts" refers to salts that largely maintain the desired pharmacologic properties of the active agents and do not trigger any undesirable toxic effects. Examples include (a) additive salts of inorganic or organic acids such as hydrochloride, hydrobromide, phosphoric acid, acetic acid, tartaric acid, oxalic acid, fumaric acid, malic acid, succinic acid, citric acid, as well as the salts of their anions; (b) salts with metal cations such as sodium, zinc, calcium, magnesium, manganese.

The preferred substances or substance categories are those with low oral bioavailability, for instance less than 30%, and with a relatively short elimination half-time value, for instance less than 3 hours. Moreover, active-agent crystals are particularly desirable.

Suitable active agents or active-agent salts may be water-soluble, or for the purpose of greater retardation they may be converted into hard-to-dissolve salts. Examples include pamoate or tannate salts of peptides or metal salt complexes of low-molecular active agents.

Examples of suitable active agents include in particular
β-lactam antibiotics such as meziocillin-sodium-monohydrate, ticarcillin-disodium, piperacillin-sodium, cefoxitin-sodium, cefotaxime-sodium, moxalatame-disodium or imipenem;
aminoglycosides such as amikacin-sulfate, neomycin, nectilmycin or gentamycin;
antiviral agents such as acyclovir-sodium; azathioprine-sodium; zidovudin, didanosin, ganciclovir or foscarnet;
antitumor agents such as bleomycin, plicamycin, mitomycin, paclitaxel, cisplatinum and carboplatinum as well as nucleoside analogues such as 5-fluorouracil, cytarabine, gemcitabine-hydrochloride, 5-azacytidine;
antiparkinsonian agents such as N-0923, levodopa, methyldopa, scopolamine-hydrobromide, tolterodine-tartrate or propargylamine derivatives, their metabolites and prodrugs of these metabolites for instance as described in WO 99/03817 and WO 99/48858;
anti-Alzheimer's agents and cholinesterase inhibitors such as neostigmine bromide, edrophonium, demecarium bromide and tacrin hydrochloride;
active agents for treating diabetic or non-diabetic neuropathy, such as metformin and dextromethorphan;
narcotics such as morphine hydrochloride, tramadol hydrochloride, alfentanyl hydrochloride, fentanyl citrate, naloxone hydrochloride and ketamine hydrochloride;
tyrosinkinase inhibitors, especially trk-inhibitors such as indolocarbazole and staurosporine;
muscarine receptor antagonists such as trihexyphenidyl hydrochloride, dicyclomine hydrochloride, oxybutinine chloride;
antiepileptics such as phenytoin sodium or harkoseride;
serotonin antagonists such as sumatriptane;
heparins and their derivatives such as heparin, enoxaparin, fraxiparin and dalteparin;
active agents for treating incontinence, such as oxybutinine hydrochloride or derivatives of the 3,3-diarylpropylamines as described in the international patent application PCT/EP99/03212;
antiarrhythmic drugs such as benzoylbenzofuran derivatives as described in WO 01/29081;
peptides such as oxytocin; vasopressin; adrenocorticotrope hormone (ACTH); growth factors such as epidermal growth factors (EGF), fibroblast growth factors (a-FGF, b-FGF, FGF-9 etc), vascular endothelial growth factor (VEGF), tumor necrose factor (TNF), platelet growth factor (PDGF), neurotrophins (NT 1–3, BDNF, NGF), erythropoietin or insulin-like growth factors (IGF); releasing factors such as luteinizing hormone-releasing hormone (LHRH), growth hormone releasing factor (GRF), gonatropin-releasing hormone (GnRH), gastrin-releasing factor or tyrosin-releasing hormone (TRH); thyroid-stimulating hormone (TSH); parathryroid hormone (PTH), luteinizing hormone (LH); follicle-stimulating hormone (FSH); somatostatin and analogues; somatotropin; gastrin; prolactin; motilin; callicrein; amylin; glucagon; glucagon-like peptide (GLP); calcitionin; calcitionin-related peptide; natriuretic proteins; angiotensins; renin; brandykinin; encephalins; endorphins; interferons (alpha, beta, gamma); chemokins; hemato-poietic growth factors such as erythropoietin; stem cell growth factors (SCF), interleukins (e.g. IL-1 to IL-12), granulocyte growth factors (G-CSF and GM-CSF) or monocyte growth factors (M-CSF); peptide antibiotics such as tyrocidin, gramicidin, bacitracin or nisin; angiopeptin; hirudin; thrombopoietin, urogastrons; osteogenic proteins such as the bone morphogenic protein, antibodies as well as their fragments and derivatives (Fab, (Fab)$_2$, diabodies, scFVs etc); transcription factors; peptide nucleic acids; vaccine peptides of viral or bacterial origin; tumor-based peptides such as PSA, PSMA, PSCA; HLA peptides or MHC antigens; leucocyte markers (e.g. CD3, CD 11a-c, CD28, CD30, Cdw52) and their ligands (e.g. B7); T-cell receptors and their fragments; angiostatic peptides such as angiostatin or endostatin; onconases; integrins and integrin-inhibiting peptides (RGDS peptides); lectins such as mistel lectin; calmodulin; vacoactive intestinal peptides (VIP); fertilization-promoting peptides (FPP); cocaine and amphetamine regulated transcript peptides (CART); leptin and its derivatives; soluble receptors; endothelin; insulin; proinsulin and C-peptide as well as their biologically active variants and fragments.

The pharmaceutical composition according to the invention may contain one or several such active agents. What is important for the retardation effect is that the active agents to be retarded are in their solid phase and are largely undissolved in the vehicle.

An active agent dissolved in the vehicle is quickly released from the formulation in the body. Combining a vehicle-insoluble agent in its solid phase with an agent contained in the vehicle in its dissolved state makes it possible to obtain fast-acting exposure to the substance coupled with a retardation effect.

Particularly preferred pharmacologically active substances are agents for the treatment of neurodegenerative ailments such as Parkinson's disease, Alzheimer disease, neuropathy or epilepsy.

Examples include N-0923, levodopa and the proinsulin C-peptide.

The term "proinsulin C-peptide" refers to the 31 amino acid linking protein from the native human C-peptide as well as to fragments and variants thereof, as disclosed in OS WO 98/13384, to the extent that these fragments and variants are suitable for the treatment of complications from diabetes and in particular for the therapy of diabetic neuropathy.

A parenteral depot application can be particularly desirable for the treatment of neurodegenerative diseases, given that because of the disease it is difficult at best to ensure frequent oral self-administration by the patient. On the other hand, non-hospitalized patients can hardly be expected to subject themselves to extended infusions with unretarded injectables that have a short half-time value.

For patients with Parkinson's disease, a frequent and characteristic symptom is morning stiffness due to the nocturnal treatment gap. For that reason as well, the administration of antiparkinsonian agents employing the depot formulation according to the invention is particularly advantageous since the continuous release of the active agent from the depots per this invention avoids a nocturnal deficiency in the therapy of the patient.

One preferred active agent for use in the formulations according to the invention is levodopa. At 1–3 hours, its half-time in the plasma is rather short. Moreover, in the case of oral administration a considerable degradation by enzymes of the gastrointestinal mucosa can be expected. While adding carbidopa or other MAO inhibitors can reduce the rate of decomposition of levodopa by monoamino oxidase (MAO), there nevertheless remains a substantial need for formulations with extended effectiveness.

According to more recent discoveries, uniform levodopa plasma levels brought about by continuous infusions have a favorable effect on the individual fluctuations, known as the on/off phenomenon, of the effectiveness of levodopa as well as on the genesis of dyskinesiae that are evidently a result of the fluctuating plasma levels in the case of oral therapy (Chase, Neurol 44, Suppl 6 (1994) p. 15).

The composition according to the invention is particularly preferred for the administration of N-0923 hydrochloride, and especially so in a formulation with crystalline N-0923 hydrochloride. The latter can be produced for instance as described in U.S. Pat. No. 4,564,628. The bioavailability of the pharmaceutical composition per the invention is about 70% for N-0923 (rotigotine) and the active agent is released from the depots in the body in a therapeutically effective amount for over 48 hours. The plasma agent levels obtained correspond in a linear relationship to the dose introduced in the body.

Suitable daily doses of rotigotine are for instance 0.5–40 mg, preferably 1–20 mg, better yet 2–15 mg and ideally 2–10 mg. The result will be plasma level rotigotines of 0.2–10 ng/ml, preferably 0.3–5 ng/ml and ideally 0.4–3 ng/ml. The administered dosage of the active agent concerned can be controlled by appropriate selection of the concentration of the agent in the formulation as well as by the volume injected. That volume can be varied over a wide range from 5 to 2000 µl. Preferred application volumes are those between 10 and 1000 µl and especially between 10 and 500 µl.

Suitable concentrations (in w/v) for the pharmacologically active substances in the formulation according to the invention are determined first of all by the therapeutic efficacy and the biocompatibility of the active agent concerned. Preferred concentration ranges are 0.01–20%, better yet 0.02–5% and ideally 0.1–2%.

Another aspect of the invention is an anhydrous pharmaceutical composition comprising at least one pharmacologically active agent in crystalline form that is essentially insoluble in the pharmaceutical composition, at least one medium-chain triglyceride and at least one polyol fatty acid monoester.

Preferred concentrations in this form of implementation are 0.02–5% for the active agent, 0.1–5% for the glycerol monoester and 88–99.8% for the medium-chain triglycerides. The preferred glycerol fatty acid monoester is glycerol monolaurate.

Finally, this invention relates to a kit comprising a pharmaceutical preparation according to the invention and an injection device. The injection device may be a system yet to be filled with said pharmaceutical composition or an injection system prefilled with the pharmaceutical composition according to the invention. The injection system may be equipped with a conventional cannula or, alternatively, it may be a needle-less injection system.

Another object of the invention is a kit containing several dosages of the pharmaceutical composition according to the invention as well as several injection devices, constituting for instance a week's or a month's supply.

Another aspect of the invention is a kit comprising a pharmaceutical composition for the injection of an antiparkinsonian agent and an oral or transdermal form of administration of an antiparkinsonian agent. An "antiparkinsonian agent" is any active agent that can favorably influence a pathologically modified dopamine metabolism and/or in some other way reduce and/or prevent in therapeutic or prophylactic fashion the progression or existence of Parkinson's disease and/or to alleviate the symptoms associated with Parkinson's disease.

Those skilled in the art are familiar with such antiparkinsonian agents. Examples of suitable additional active agents, non-limiting for the purpose of this application, include representatives of the group of metabolic dopamine precursors, dopamine receptor agonists, dopamine transport blockers, MAO inhibitors, muscarine receptor antagonists, glutamate receptor antagonists, catechol-O-methyl transferase blockers, neurotrophines, immunophilin ligands, histamine antagonists, antioxidants, glutathion transferase activators, anti-apoptose agents or calcium antagonists.

Suitable representative examples include, in particular, levodopa, methyldopa, biperiden, paragyline, rasagiline, selegiline, lisuride, pergolide, bromocriptine, cabergoline, benzatropin, ropinirole, amantadine, memantine, trihexyphenidyl, diphenhydramine, dihydroergocryptine, tolcapone, entacapone, metixene, procyclidine, budipine, bornaprine, pramipexole, glial cell line-derived neurotrophic factor (GDNF) and the brain-derived neurotrophic factor (BDNF).

A kit that contains an injectable antiparkinsonian formulation and an oral form of administration of the antiparkinsonian agent may be beneficial for instance by preventing or bridging an excessive drop of the plasma levels when one depot is exhausted and before a new depot is applied or becomes effective.

Therefore, one particularly preferred form of implementation is constituted of a kit including an injectable depository form of an antiparkinsonian agent and an oral, fast-acting formulation of the same or some other antiparkinsonian agent. Examples of such fast-acting oral dosaging forms have been covered in prior art and have been described for instance in EP A 651 997.

IMPLEMENTATION EXAMPLES

1. Production and Crystallization of N-0923

N-0923 is produced and crystallized as described in U.S. Pat. No. 4,564,628.

2. Production of an N-0923 Suspension containing 1% N-0923 and 1% GML (a) Producing the Continuous Phase 1411.2 g Miglyol 812 was weighed into a Duran vial. 14.4 g Imwitor 312 was added to the miglyol and then heated for 30 minutes to 80° C. under simultaneous agitation. The clear solution was cooled down to room temperature and filtered.

(b) Producing the Suspension 1188 g of the solution produced per (b) above was transferred into a lab-type glass reactor, 12 g of N-0923 was added and homogenized in a nitrogen atmosphere for 10 minutes using an Ultraturrax at 10,000 RPM. With the Ultraturrax running (at 2,000 RPM), the suspension was filled into brown glass vials.

3. Production of an N-0923 Suspension Containing 0.5, 1.5 and 2% N-0923 and 0.5%, 1% or 1.5%

The suspension was produced as described in 1. above except with suitably modified quantities.

4. Thermal Sterilization of N-0923

A 0.6% aqueous solution of N-0923 hydrochloride (preparation I) and a 1% N-0923 suspension per implementation example 2 (preparation II) were autoclaved for 20 minutes at 120° C. and 0.2 Pa. In addition, a 0.5% aqueous N-0923 solution (preparation III) was autoclaved in a nitrogen atmosphere. Subsequently the degradation rates were determined by photometry.

It was found that in the autoclaving of the aqueous solutions of preparations I and III, 1.5% of the N-0923 had in each case thermally disintegrated into decomposition products. By contrast, preparation II had decomposed by less than 0.5%.

5. Release of N-0923 from the Depot per this Invention in a Rat

Sprague-Dawley rats were given subcutaneous bolus injections of an oily N-0923 crystalline suspension of the following composition:

| N-0923: | 0.5 or 1% |
|---|---|
| Imwitor 312: | 1% |
| Miglyol 812: | at 100% |

The following dosages were applied every 48 hours:
1 mg/kg (0.2 ml/kg of a 0.5% suspension)
3 mg/kg (0.6 ml/kg of a 0.5% suspension)
10 mg/kg (1 ml/kg of a 1% suspension)
30 mg/kg (3 ml/kg of a 1% suspension)

Figure 1A:
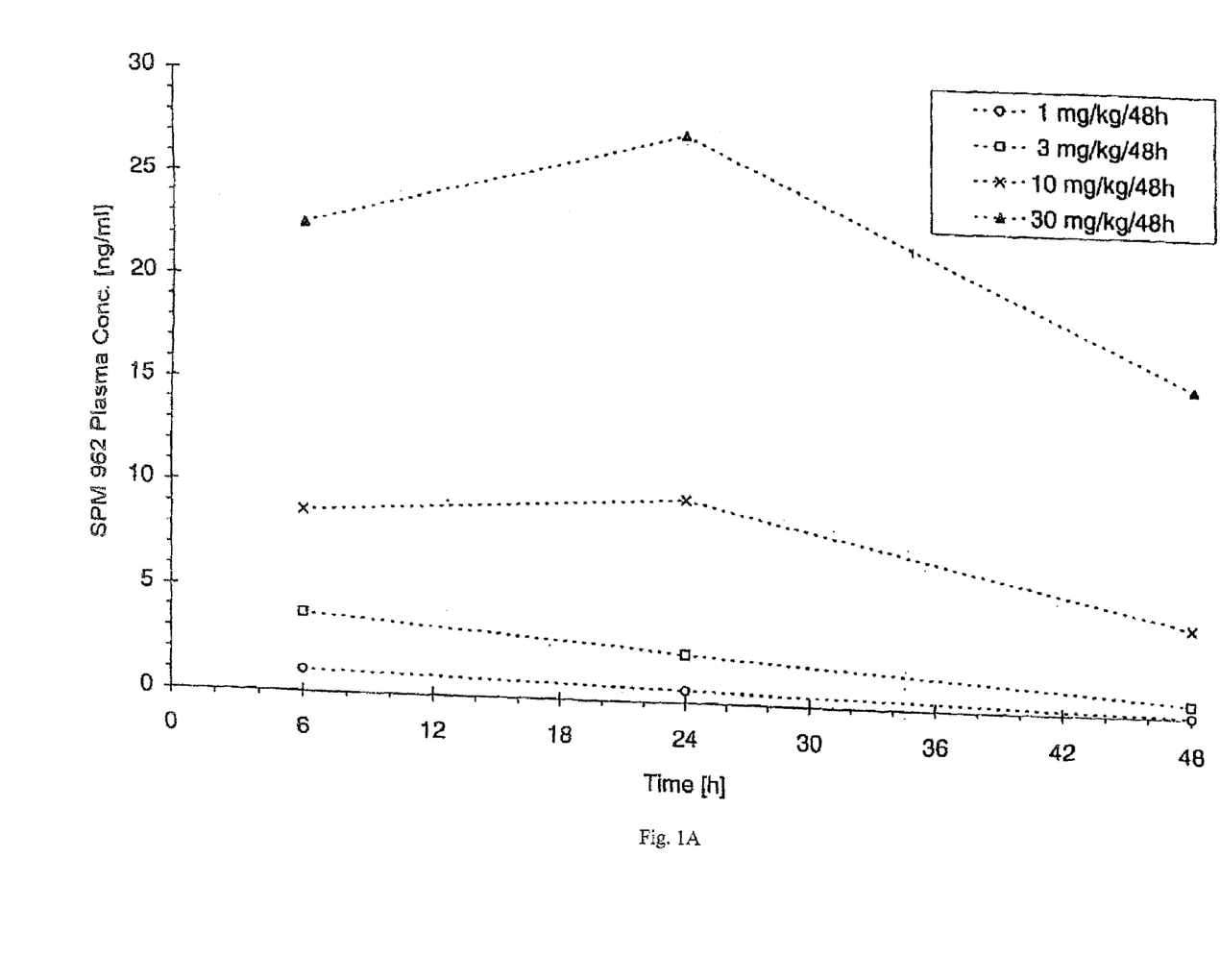
Figure 1B:
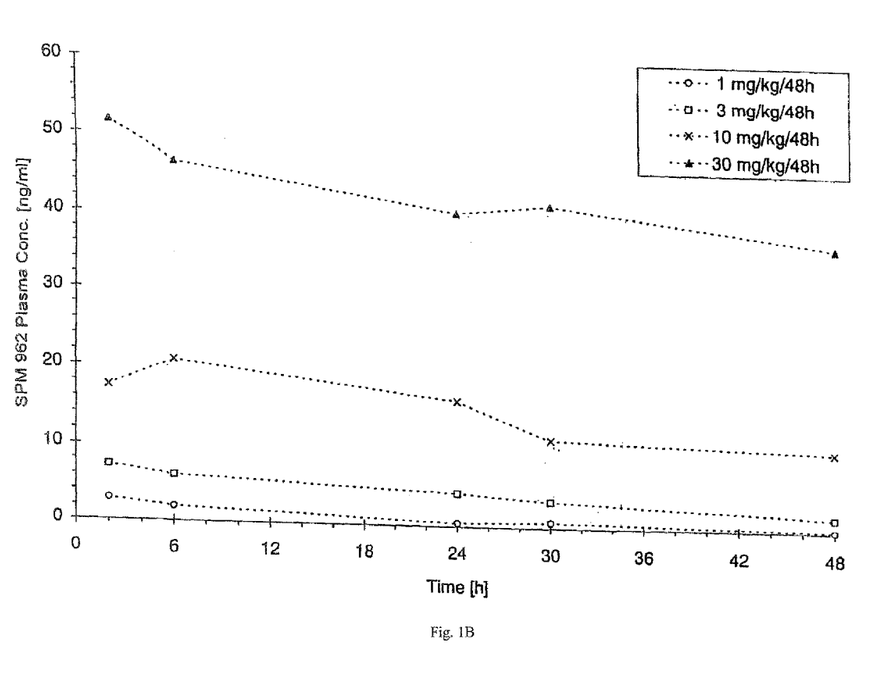

6, 24 and 48 hours after the $2^{nd}$ and $46^{th}$ administration plasma samples were taken and the N-0923 concentration was analyzed using LC-MS-MS. The readings from 6 animals were averaged. The results are shown in FIG. 1.

6. Release of N-0923 from the Depots per this Invention in the Rat

The test conditions were identical to those in implementation example 5 except that every 48 hours a dose of 12.5 mg N-0923 per kg body weight was applied.

Figure 2:
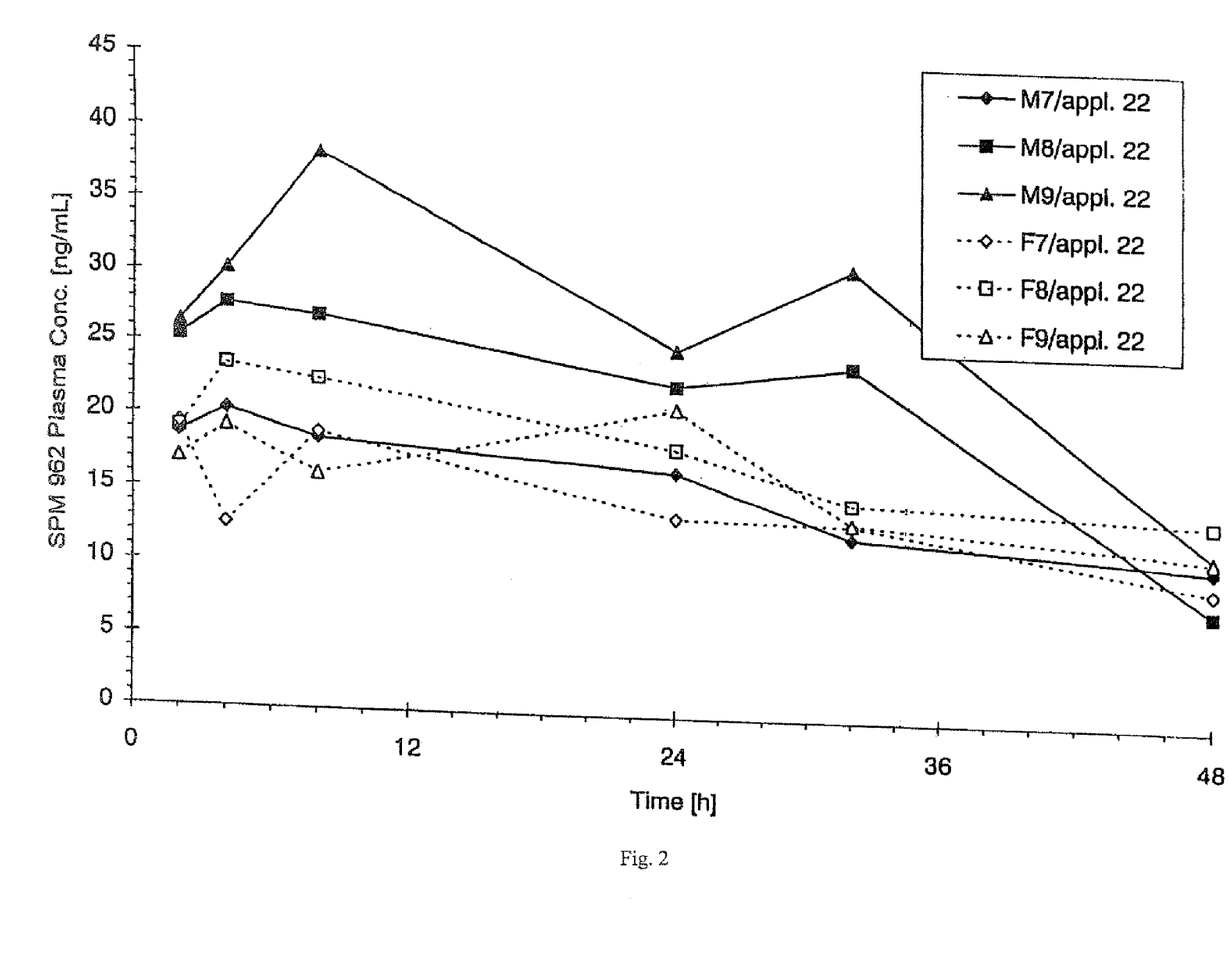
FIG. 2 shows N-0923 plasma concentrations in a rat after the subcutaneous administration of 12.5 mg N-0923N per kg body weight. The preparation was administered every 48 hours. The plasma levels of individual animals were recorded respectively 2, 4, 8, 24, 32 and 48 hours after the $22^{nd}$ application.

Readings were taken 2, 4, 8, 24, 32 and 48 hours after the 22nd application and were quantified. The plasma levels of the individual animals are shown in FIG. 2.

7. Release of N-0923 from the Depots per this Invention in the Monkey

Cynomolgus monkeys were given daily subcutaneous bolus injections of oily N-0923 crystalline suspensions of the following composition:

| N-0923: | 0.5 or 1% |
|---|---|
| Imwitor 312: | 1% |
| Miglyol 812: | at 100% |

The application was performed daily in dosages of 0.25, 1 and 4 mg/kg. 2, 6 and 24 hours after the $3^{rd}$ and $85^{th}$ application plasma samples were taken and analyzed using LC-MS-MS.

Figure 3A:
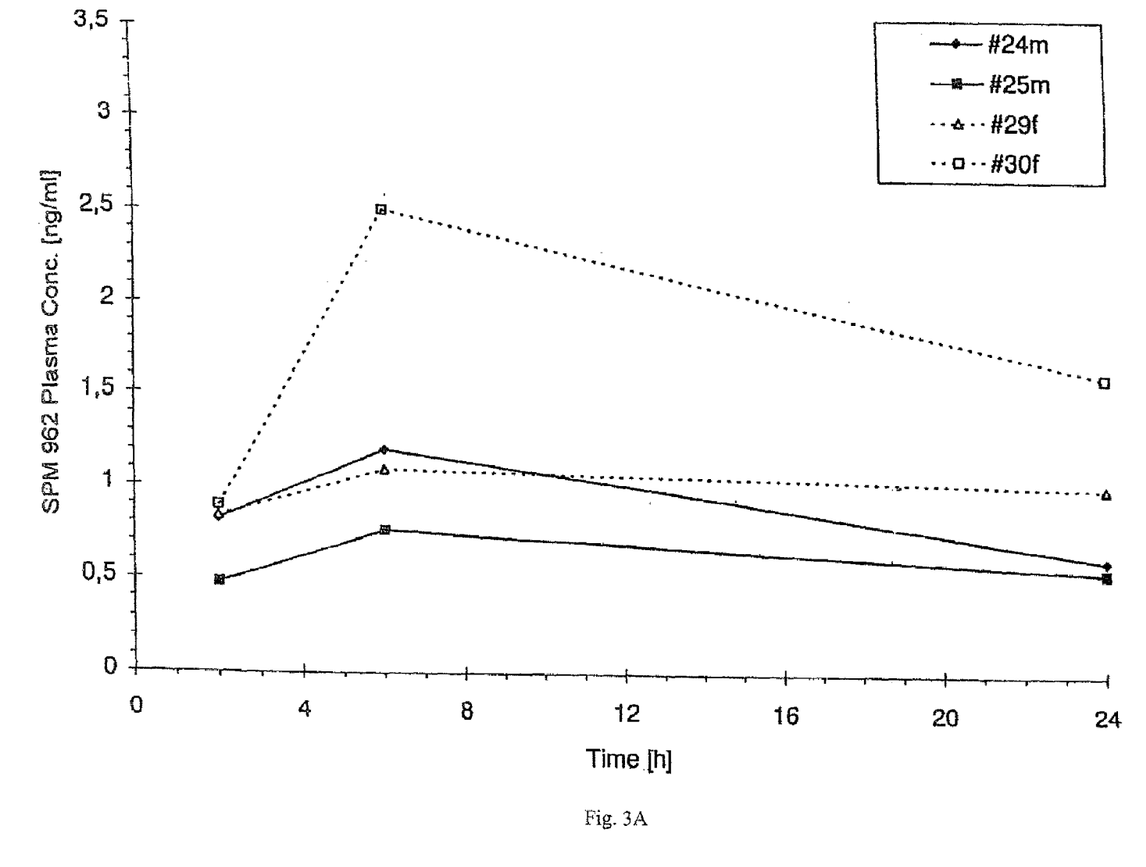
FIG. 3A shows N-0923 plasma concentrations in a monkey after 85 applications of 1 mg/kg N-0923 in the form of an oily N-0923 crystal suspension.
Figure 3B:
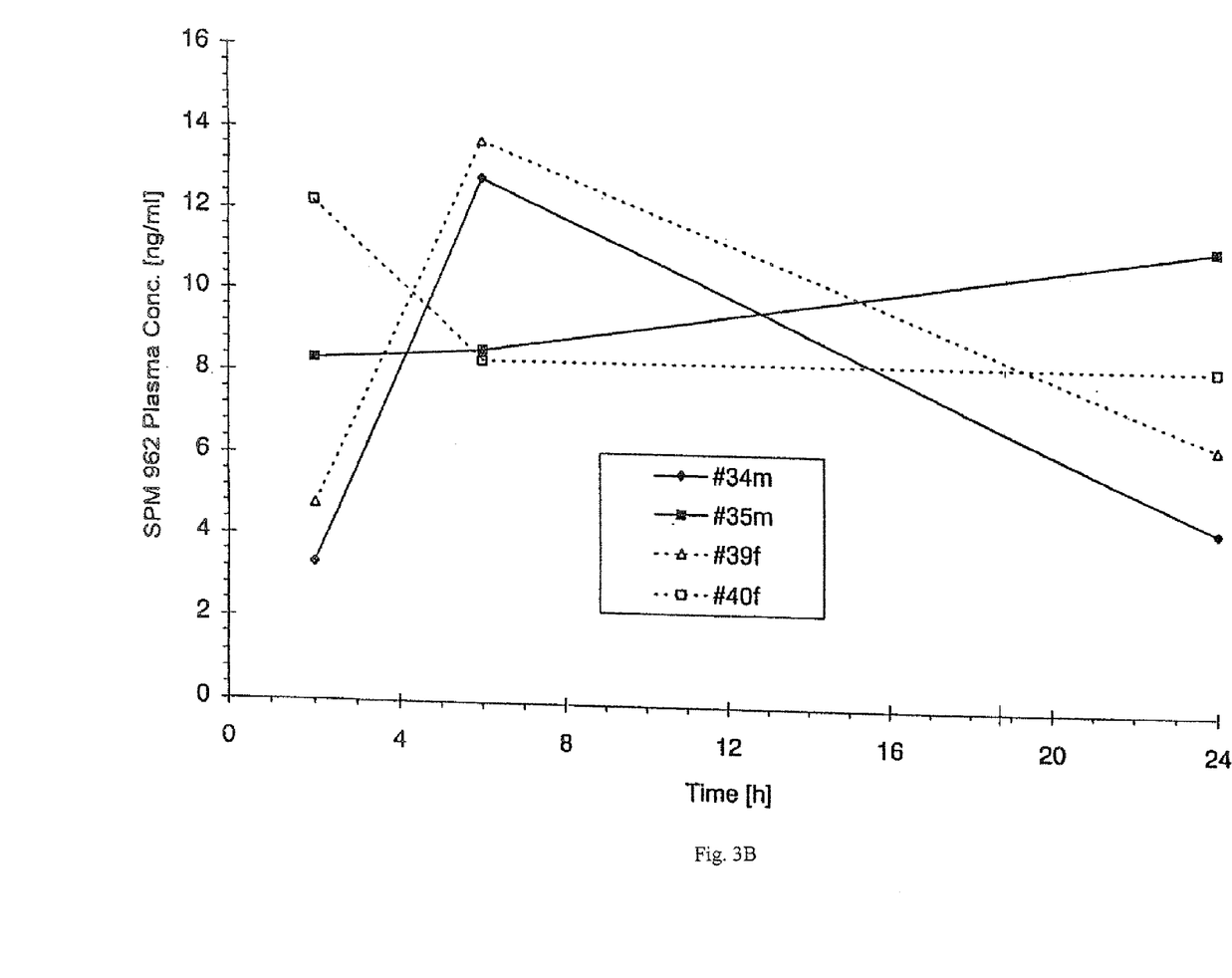
FIG. 3B shows N-0923 plasma concentrations in a monkey after 85 applications of 4 mg/kg N-0923 in the form of an oily N-0923 crystal suspension.
Figure 4:
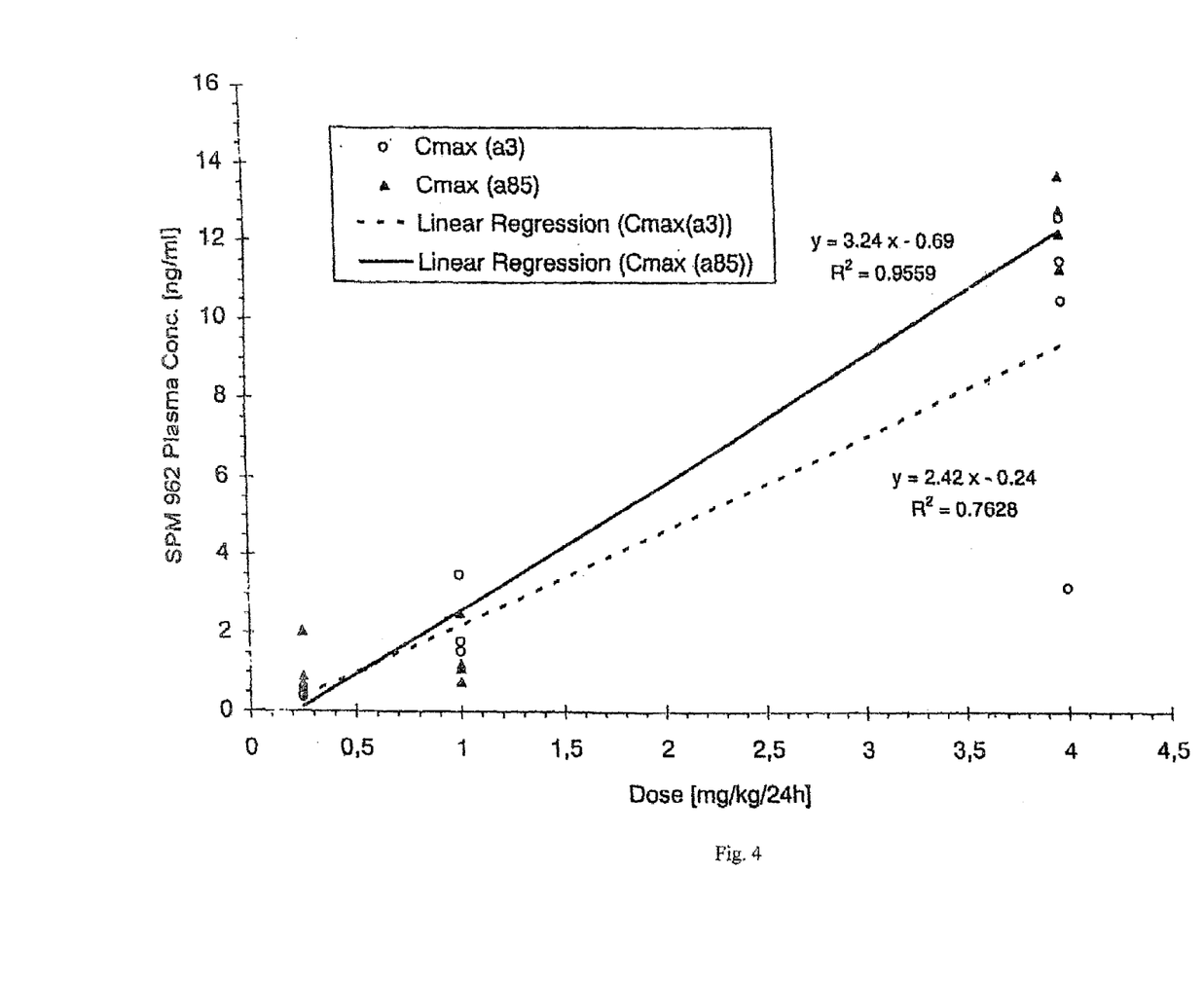
FIG. 4 depicts the correlation in a monkey between an applied dose of N-0923 in the form of oily crystal suspensions and the maximum plasma level after a 3-time and an 85-time daily application.

FIG. 3 shows the readings for the individual animals. FIG. 4 shows the relationship between the dose applied and the resulting maximum plasma concentrations.

The invention claimed is:

1. An injectable pharmaceutical composition comprising:
   (a) at least one pharmacologically active agent in its solid phase;
   (b) a vehicle essentially consisting of polyol fatty acid esters with an esterification level of over 80%; and
   (c) a wetting agent comprising polyol fatty acid esters with a monoester content of over 60%,
   wherein the active agent is an antiparkinsonian agent which is released in the body from the injectable pharmaceutical composition in a therapeutically effective amount over a time period of at least 24 hours.

2. The injectable pharmaceutical composition of claim 1, wherein the vehicle is more than 70% (w/w) of the total composition.

3. The pharmaceutical composition of claim 1 or 2 wherein the pharmaceutical composition is anhydrous.

4. The pharmaceutical composition of claim 1 or 2 wherein the pharmacologically active agent is substantially insoluble in the pharmaceutical composition.

5. The pharmaceutical composition of claim 1 or 2 wherein the vehicle consists essentially of polyol fatty acid esters containing as the polyol component 1,3-propanediol, 1,3-butanediol or glycerol.

6. The pharmaceutical composition of claim 1 or 2 wherein the vehicle consists essentially of polyol fatty acid esters containing over 90% saturated fatty acids.

7. The pharmaceutical composition of claim 1 or 2 wherein the vehicle consists essentially of polyol fatty acid esters containing fatty acids with a chain length of 6 to 14 C-atoms.

8. The pharmaceutical composition of claim 1 or 2 wherein the vehicle consists essentially of medium-chain triglycerides.

9. The pharmaceutical composition of claim 1 or 2 wherein the wetting agent consists essentially of polyol fatty acid esters containing as the polyol component 1,3-propanediol, glycerol, 1,2,3-butanetriol, 1,2,4-butanetriol, 1,3-butanediol, sorbitan or isopropanol.

10. The pharmaceutical composition of claim 1 or 2 wherein the wetting agent consists essentially of polyol fatty acid esters containing over 90% saturated fatty acids.

11. The pharmaceutical composition of claim 1 or 2 wherein the wetting agent consists essentially of polyol fatty acid esters containing fatty acids with a chain length of 6 to 14 C-atoms.

12. The pharmaceutical composition of claim 1 or 2 wherein the wetting agent consists essentially of glycerol monolaurate or glycerol monocaprylate.

13. The pharmaceutical composition of claim 1 or 2 wherein the wetting agent is present at a concentration of 0.1–5% (w/w).

14. The pharmaceutical composition of claim 1 or 2 wherein the pharmaceutical composition is free of any phosphatides.

15. The pharmaceutical composition of claim 1 or 2 wherein the pharmacologically active agent is present in crystalline form.

16. The pharmaceutical composition of claim 1 or 2 wherein the pharmacologically active agent is present in an amorphous form.

17. The pharmaceutical composition of claim 1 or 2 wherein the pharmacologically active agent is present in salt form.

18. The pharmaceutical composition of claim 1 wherein the active agent is present at a concentration of from 0.01 to 20% (w/v).

19. The pharmaceutical composition of claim 1 wherein the active agent is present at a concentration of from 0.02 to 5% (w/v).

20. The pharmaceutical composition of claim 3 wherein the active agent is selected from the group consisting of N-0923 (rotigotine), levodopa, cabergoline, ropinirole, pergolide and pramipexole.

21. The pharmaceutical composition of claim 1 or 20 wherein the composition consists of (a) the at least one pharmacologically active agent in its solid phase; (b) the vehicle consisting essentially of polyol fatty acid esters with an esterification level of over 80%; and (c) the wetting agent comprising polyol fatty acid esters with a monoester content of over 60%.

22. The pharmaceutical composition of claim 1 or 20 wherein the composition does not contain a fatty acid aluminum salt.

23. A kit comprising:
(a) a pharmaceutical composition of claim 1 or 2; and
(b) an injection device.

24. The pharmaceutical composition of claim 2 wherein the active agent is present at a concentration of from 0.01 to 20% (w/v).

25. The pharmaceutical composition of claim 2 wherein the active agent is present at a concentration of from 0.02 to 5% (w/v).

26. The pharmaceutical composition of claim 2 wherein the active agent is selected from the group consisting of N-0923 (rotigotine), levodopa, cabergoline, ropinirole, pergolide and pramipexole.

27. The pharmaceutical composition of claim 2 wherein the composition consists of (a) the at least one pharmacologically active agent in its solid phase; (b) the vehicle consisting essentially of polyol fatty acid esters with an esterification level of over 80%; and (c) the wetting agent comprising polyol fatty acid esters with a monoester content of over 60%.

28. The pharmaceutical composition of claim 2 wherein the composition does not contain a fatty acid aluminum salt.

29. The pharmaceutical composition of claim 1 wherein the active agent is selected from the group consisting of N-0923 (rotigotine), levodopa, cabergoline, ropinirole, pergolide and pramipexole.

* * * * *

UNITED STATES PATENT AND TRADEMARK OFFICE
CERTIFICATE OF CORRECTION

| | | |
|---|---|---|
| PATENT NO. | : 7,309,497 B2 | Page 1 of 1 |
| APPLICATION NO. | : 10/344863 | |
| DATED | : December 18, 2007 | |
| INVENTOR(S) | : Stephan Rimpler et al. | |

It is certified that error appears in the above-identified patent and that said Letters Patent is hereby corrected as shown below:

On Title Page
Item 54 and Col. 1, Line 2
In the title, "SYSTEMATIC" should read --SYSTEMIC--.

Signed and Sealed this

Twenty-ninth Day of April, 2008

JON W. DUDAS
*Director of the United States Patent and Trademark Office*